US008603825B2

(12) United States Patent
Chua et al.

(10) Patent No.: US 8,603,825 B2
(45) Date of Patent: Dec. 10, 2013

(54) SENSOR FOR MEASURING GAS PERMEABILITY OF A TEST MATERIAL

(75) Inventors: Soo Jin Chua, Singapore (SG); Senthil Kumar Ramadas, Singapore (SG); Xinbo He, Clemson, SC (US)

(73) Assignee: Agency for Science, Technology and Research, Centros (SG)

( * ) Notice: Subject to any disclaimer, the term of this patent is extended or adjusted under 35 U.S.C. 154(b) by 849 days.

(21) Appl. No.: 10/594,789

(22) PCT Filed: Mar. 31, 2004

(86) PCT No.: PCT/SG2004/000075
§ 371 (c)(1),
(2), (4) Date: Jul. 18, 2007

(87) PCT Pub. No.: WO2005/095924
PCT Pub. Date: Oct. 13, 2005

(65) Prior Publication Data
US 2007/0292957 A1    Dec. 20, 2007

(51) Int. Cl.
*G01N 15/08* (2006.01)
*B01J 19/00* (2006.01)

(52) U.S. Cl.
USPC ............................. 436/5; 422/82.02; 427/58

(58) Field of Classification Search
USPC ............................. 436/5; 427/58; 422/82.02
See application file for complete search history.

(56) References Cited

U.S. PATENT DOCUMENTS

| | | | |
|---|---|---|---|
| 4,595,485 A * | 6/1986 | Takahashi et al. | ............ 204/406 |
| 6,067,840 A | 5/2000 | Chelvayohan et al. | |
| 6,325,979 B1 | 12/2001 | Hahn et al. | |
| 6,460,405 B1 | 10/2002 | Mayer et al. | |
| 6,567,753 B2 | 5/2003 | Potyrailo | |
| 7,004,010 B2 | 2/2006 | Larsen et al. | |
| 2003/0203210 A1 * | 10/2003 | Graff et al. | .................... 428/412 |

FOREIGN PATENT DOCUMENTS

| | | |
|---|---|---|
| DE | 10208767 C1 | 7/2003 |
| FR | 2762679 B1 | 10/1998 |
| JP | 09-026403 A1 | 1/1997 |
| TW | 518772 B | 1/2003 |
| WO | 02079757 A2 | 10/2002 |
| WO | WO-03/094256 A2 | 11/2003 |

OTHER PUBLICATIONS

Rim, J., & Yun, S. Ultrasonic Velocity and Absorption in Binary Solutions of Silicon Dioxide and Water.(1998). Japanese Journal of Applied Physics. 37: 2801-2802.*

Kumar, R.S., et al., Low moisture permeation measurement through polymer substrates for organic light emitting devices , Thin Solid Films, Sep. 30, 2002, pp. 120-126, vol. 417, No. 1-2.

(Continued)

*Primary Examiner* — Krishnan S Menon
*Assistant Examiner* — Rebecca M Fritchman
(74) *Attorney, Agent, or Firm* — Hultquist, PLLC; Steven J. Hultquist

(57) ABSTRACT

A sensor for measuring gas permeability of a test material, comprising: an electrically conductive sensing element that comprises a water and/or oxygen sensitive material, wherein the reaction of said material with water or oxygen when the sensing element is contacted with water and/or oxygen results in a change in the electrical conductivity of the sensing element, and two electrodes electrically connected to the sensing element.

28 Claims, 9 Drawing Sheets

(56) References Cited

OTHER PUBLICATIONS

Nisato, G. et al., Evaluating High Performance Diffusion Barriers: the Calcium Test , International Display Workshop, Oct. 2001.

Paetzold, R., et al., "Permeation rate measurements by electrical analysis of calcium corrosion", "Review of Scientific Instruments", 2003, pp. 5147-5150, vol. 74, No. 12.

* cited by examiner

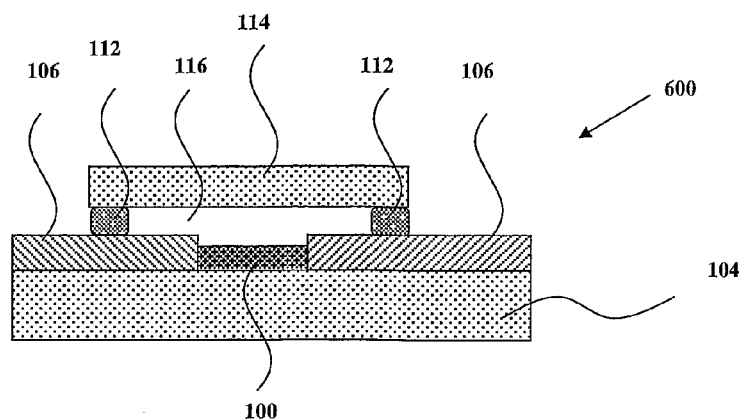
FIGURE 6
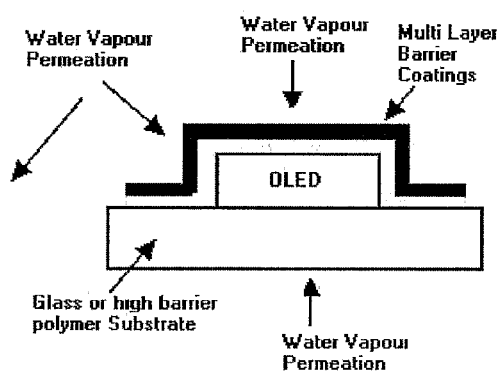
METHOD-A
FIGURE 7A
METHOD-B
FIGURE 7B

Barrier polymer substrate coated with liner layer

1.1 Ohms @     4.5 Ohms @     6.5 Ohms @
0 hours            2 hours            4 hours Images (10x magnification) of calcium sensor show uniform oxidation at different time intervals and resistance – Figure 4a

Barrier polymer substrate with out liner layer

Example image (10x magnification) of non-uniform oxidation – Figure 4b

| 1.13 ohms @ | 1.15 ohms @ | 3.9 ohms @ | 88 ohms @ |
| 0 hour | 120 hours | 168 hours | 216 hours |

Calcium sensor oxidation pattern – shows uniform oxidation at different time intervals and resistance – Figure 6

SENSOR FOR MEASURING GAS PERMEABILITY OF A TEST MATERIAL

PRIORITY CLAIM AND CROSS-REFERENCE TO RELATED APPLICATION

This application is filed under the provisions of 35 U.S.C. §371 and claims the benefit of priority of International Patent Application No. PCT/SG2004/000075 filed Mar. 31, 2004. The disclosure of said International Patent Application is hereby incorporated herein by reference, in its entirety.

The invention relates to a sensor for measuring gas permeability of a test material, a method of producing a sensor, and a gas permeability measurement system. The invention also relates to a method of determining gas permeability through a test material.

The emergence of new technologies in the electronics and biomedical fields in recent years has prompted the parallel development of new materials and structures.

One example of such a technology is the flexible flat panel display which uses flexible organic light emitting devices (FOLED). Each FOLED comprises materials and structures having electrical, mechanical and optical properties that allow for large area displays. However, FOLED architectures comprise organic electroluminescent materials and cathodes that are susceptible to damage from reaction with water vapour and oxygen in the atmosphere. Therefore, FOLED displays require high barrier substrates, sealants and encapsulation materials, which are extremely impermeable to water and oxygen in order to attain the industry standards specified for its minimum lifetime.

Another technology which requires water and oxygen sensitive materials can be found in the area of memory storage, particularly in the hard disk drive industry. The material used in hard disk platters comprise metal or metal oxide which can be degraded by oxygen. In order to maintain the integrity of magnetic data, packaging structures and materials must provide low levels of gas permeation in order to prevent the degradation of the seal and metal oxide in the platter.

Other examples of applications which require the use of materials that provide gas barrier properties include hermetically sealed packages found in food, drug and biological sample packages. In addition, sealants, plastics and composite materials are also often required to have gas barrier properties.

More recently, applications have been developed that require materials and structures possessing very low gas permeability. These materials and structures have in turn necessitated the use of sensitive measurement instruments, in particular gas sensors, which can assess gas permeation properties at very low gas permeation levels.

One class of sensors rely on detection methods which do not involve chemical reaction with the target gas. U.S. Pat. No. 6,067,840 issued to Texas Instruments Inc. discloses an optical infrared (IR) gas sensor. The differential absorption between two IR sources, each directed to a target gas and a reference gas, is used to determine the concentration of a gas being monitored.

U.S. Pat. No. 6,460,405 issued to MOCON, Inc. discloses a gas sensor in which a test specimen is exposed to a chemically inert tracer gas, such as helium or carbon dioxide. A tracer gas detector is provided to measure the flow of tracer gas through the specimen and the measurements are correlated to the gas permeability of the test specimen.

U.S. Pat. No. 6,567,753 discloses a sensor for determining barrier properties of a barrier coating with respect to a plurality of fluids. A dual-response acoustic wave transducer is coated with the barrier coating and exposed to the plurality of fluids. The permeation of the fluid or dissolution of the coating is subsequently measured using acoustic wave and optical detection measurements.

Another class of sensors utilise sensing elements which react with the target gas. Kumar et al. (Thin Solid Films 417, 2002, 120-126) discloses a low moisture permeation sensor that relies on the optical measurement of corrosion on the surface of calcium films. The calcium film is initially a highly reflective metallic surface. As water vapour and oxygen progressively react with the calcium film, the reflective surface gradually turns into an opaque film. The test specimens are photographed at regular intervals to monitor the change in transmission property of the calcium films. By subjecting the photographs of the calcium film to analysis using image analysis software, the change in optical properties of the calcium film is correlated to the flow rate of water vapour into the encapsulation structure. This type of sensor is also disclosed in G. Nisato et al., Evaluating High Performance Barrier Films, International Display Workshop, October 2001.

One drawback of the currently available gas sensors is their inability to measure gas permeation at a sufficiently high level of sensitivity required for assessing very low gas permeability materials. For instance, the industry standard specified for the lifespan of FOLED devices is more than 10,000 operating hours. In order to attain this lifespan, oxygen and water vapour transmission rates through the encapsulation structures of FOLED devices should be below $10^{-5}$ g/m$^2$/day and $10^{-6}$ cc/m$^2$/day respectively (at 38° C. and 95% relative humidity). However, available instruments have sensitivity limits of around $10^{-3}$ g/m$^2$/day for water and about $10^{-3}$ cc/m$^2$/day for oxygen.

Another drawback of the currently available gas sensors is that the service temperature is limited to moderate temperatures of typically about 50° C. With a low temperature limitation, performance tests cannot be carried out under conditions for bringing about accelerated gas permeation, thereby resulting in long test durations which are uneconomical to carry out.

Accordingly, it is an objective of the present invention to overcome disadvantages of currently known sensors. It is a further objective of the invention to provide a sensor which has high sensitivity, good spatial and time resolution, high service temperature, but is still economical to manufacture and use. This objective is solved by a sensor and a respective method of producing the sensor having the features as specified in the independent claims. Such a sensor of the present invention is a sensor for measuring gas permeability of a test material comprising:

an electrically conductive sensing element that comprises a water and/or oxygen sensitive material, wherein the reaction of said material with water or oxygen when the sensing element is contacted with water and/or oxygen results in a change in the electrical conductivity of the sensing element, and two electrodes electrically connected to the sensing element.

The invention is based on the discovery that gas permeation measurements that are performed on materials and structures such as low gas permeability materials can be made significantly more sensitive by monitoring the electrical and, optionally, noise properties of the gas sensor during the course of the measurement. Accordingly, the gas sensor of the present invention comprises an electrically conducting sensing element that is also sensitive either to water or oxygen alone, or to both water and oxygen. In addition, the sensing element functions as an electrical resistor which has optical, electrical and noise properties that change as it gradually reacts with water and/or oxygen during a measurement test. This change permits the rate of permeation (under steady state conditions) of moisture through the low gas permeability polymer substrates to be determined directly by physical evidence of chemical reaction of water vapour with a sensor, for example by optical measurement techniques. Alternatively, other methods such as 1/f noise spectrum measurement and resistance of the sensor can be employed to monitor sensor degradation. From these measurements, the rate of change of calcium thickness with respect to time and thus gas transmission rates across the test specimen may be derived.

The use of the sensor of the present invention in gas permeation measurements has several advantages. Firstly, the present sensor can measure gas transmission rates with high sensitivity of better than $10^{-8}$ g/m² day, and provides better time resolution as well as low percentage of error. Accordingly, it is suitable for assessing the gas permeation properties of polymer substrates, barrier coated films, or multi-layer barrier stacks which have low gas permeability properties. Secondly, the present invention provides for the measurement of combined transmission rates of oxygen and water vapour within a single test, meaning that the measurement of water vapour transmission rate (WVTR) and oxygen transmission rate (OTR) can be carried out in a single instrument console. Thirdly, transport coefficients such as the permeability coefficient, diffusion coefficient and solubility coefficient can be simultaneously determined in one test.

In the context of the invention, the term "target gas" refers to the gas which a test material or test structure is exposed to in order to measure the rate of transmission of the gas through that material or structure. The term includes individual gases such as oxygen or water vapour, and simple or multi-component mixtures thereof with nitrogen, carbon dioxide, hydrogen and sulphur dioxide, for example. Examples of multi-component mixtures include air and exhaust gases.

The terms "test material", "test structure" and "test specimen" are used interchangeably to refer to the material/structure that is being tested for its gas permeability properties using a gas sensor of the present invention.

The sensing element can comprise any suitable electrically conductive material which is sensitive to oxygen and/or water. This means that the material can be sensitive either to water alone, or oxygen alone, or both water and oxygen. Suitable materials include metals, metal alloys, metal oxides, conductive polymers, as well as mixtures and combinations thereof.

In principle, all metals that can react with water and oxygen can be used as the sensing element or within the sensing element. Such metals include highly reactive metals such as the Group I elements (for example, sodium and potassium), moderately reactive metals such as Group II elements (magnesium, calcium, barium) and transition metals such as iron, tin and chromium. Particularly suitable metals are calcium and magnesium. Apart from being reactive towards water and oxygen, they also can be readily processed into any suitable shape and dimension, such as blocks, strips or thin films.

Examples of conductive polymers which are contemplated for use within or as the sensing element include conjugated organic polymers, conjugated metallopolymers (inorganic polymers) and redox polymers. Examples of useful conducting polymers include polyaniline, polypyrrole, polythiophene, polyacetylene, poly-p-phenylene, and polyvinylpyridine, thiophene-bipyridine copolymers, polypyridine, polybipyridine, and organometallic polyphenylenes.

Examples of metal oxides which are contemplated for use as or within the sensing element include $VO_2$, $CrO_2$, $MoO_2$, and $LiMn_2O_4$; transparent conductive oxides such as cadmium stannate ($Cd_2SnO_4$), cadmium indate ($CdIn_2O_4$), zinc stannate ($Zn_2SnO_4$ and $ZnSnO_3$), and zinc indium oxide ($Zn_2In_2O_5$). No particular restriction is placed on the crystal structure of an oxide that is used, which can be either crystalline, nanocrystalline, or amorphous, for example.

The sensing element can also be formed from mixtures and combinations of the above materials. For example, it is possible to form a sensing element composition from a solution containing a suitable organic polymer and metallic particles, such as iron or calcium particles.

In order to carry out a measurement test, the sensor can be deployed in several ways. For example, the sensor may be embedded within or formed (deposited) on a surface of the test material. Alternatively, if an encapsulated environment is to be assessed, the sensor can be placed within the encapsulated environment. The test material and the accompanying sensor is then exposed to an atmosphere containing the target gas which is reactive towards the sensing element. A predetermined quantity of the sensing element is used for the measurement, and the time taken for the sensing element to be partially or completely reacted can be determined. One possible way to do so is to measure the change in current flow over a period of time, and then calculate the projected time taken for the sensing element to be fully reacted. Another possible way is to monitor the ceasing of current flow through the sensor. For example, when the current flow ceases, the sensing element may be assumed to have reacted completely.

In principle, the sensing element is able to operate at any thickness, as long as a sufficient period of time has elapsed for a sufficient quantity of the target gas to diffuse through the test material and to react with the sensing element. However, when measuring low levels of gas permeation, the sensing element may comprise of small quantities of the sensitive material in order to keep the measurement test duration within a reasonable length of time. For this reason, the thickness of the sensing element can be designed to be in the micrometer or nanometer range. For the purpose of measuring low gas permeability materials, the sensing element may have thicknesses ranging from 10 nm to 10 microns, preferably 50 nm to 1 μm and in some cases more preferably between 120 nm to 500 nm. The other dimensions of the sensing element such as length and width may be varied according to the size, shape, type and requirements of the test sample.

Some design principles can be applied to the present the sensing element. Firstly, the sensing element should preferably possess electrical properties that are low or close enough to the bulk properties of the sensing material. Secondly, the minimum thickness (H), length (L) and width (W) of the sensing elements can be optimised with measured electrical properties. In this regard, the area of the sensing element (L×W) may depend on the test substrate size as well as the experimental design for carrying out the measurement test. For example, sufficient space needs to be allocated for the encapsulation and for conductive tracks. It should be noted that one or more sensing elements may be used with a single test substrate. Each sensing element can either be in the shape of a square, rectangle, multiple stripes or any other desired shape in order to detect the permeability at the different locations on the item being tested. Furthermore, the minimum size (area) of the sensing element can also be influenced by factors such as the electrical properties of the sensor, while the maximum size (area) can also be influenced by factors such as substrate dimension and experimental design.

In one specific embodiment in which calcium is used as material for the sensing element, an optimal dimension for the calcium sensing element is about 1 cm length, about 2 cm width & about 150 nm thickness. The measured resistance of the sensor formed with this sensing element is about 0.37 Ω-cm, and is thus close to the bulk calcium sensing element's resistance of 3.41 Ω-cm. The two metal tracks that are used as electrodes in this embodiment have a dimension of about 2 cm by 2 cm. The cover glass (about 3.5 cm×about 3.5 cm) used in this embodiment for the encapsulation and rim-sealing (adhesive) width is about 2 mm.

In the invention, the sensing element is provided with electrodes (electrical connectors) to provide a means to couple the sensing element to a voltage source. Electrodes can assume any suitable shape, size or form, such as a conventional insulated copper wire, metal plates or thin film conductive tracks. The electrodes can comprise any type of electrically conductive material, commonly used materials being metals, metal oxides or mixtures thereof. The materials used here are preferably unreactive towards reactive gases comprised in the target gas, such as water and oxygen, under test conditions so that the accuracy of the sensor is not adversely affected during the course of the test. Nevertheless, metals that are reactive with these reactive gases may be used if their reaction rate with such gases is much slower than the reaction rate of the sensing element with the reactive gases. If such metals are used, it is also possible that they are provided with a protective material prior to such use. This can be achieved, for example, by surface treating the metal with an inert protective coating. This ensures that the electrical resistance of the electrodes is not affected during the course of the test.

If the sensor is used to test low gas permeability materials, it is preferable that the electrodes comprise materials that are suited for use with deposition equipment that are used in the manufacture of such sensors. Suitable materials include as metals, metal alloys, and metal oxides. Examples of metals that are suitable include silver, copper, gold, platinum, titanium, nickel, aluminium, lead and tin and their alloys. Alloys such as aluminium alloys, or iron/nickel, iron/chromium or iron/cobalt alloys can also be used in the invention. In addition, oxides with good electrical conductivity such as indium tin oxide, aluminium zinc oxide and indium zinc oxide, can be used as well. Any mixture or combination of these materials may also be used.

The electrical connection between the two electrodes and the sensing element can be formed using any suitable means of connection. For example, it is possible to adhere the electrodes to a surface of the sensor using a conductive tape or to solder the electrodes to the sensing element using a low resistance soldering metal e.g. tin. Alternatively, conductive bond pads can also be applied onto the sensing element on which the electrodes can be connected.

In one embodiment, the sensor comprises a base substrate that supports the sensing element. A base substrate facilitates the prefabrication, packaging, handling and transporting of the sensor. For instance, the base substrate can provide a suitably large surface area on which auxiliary electrical connections to the electrodes, e.g. bond pads, can be formed. The base substrate can take a variety of forms, such as a PVC board, a PET sheet or an adhesive film that is attachable to a test specimen.

In principle, any material that is inert towards any reactive gas present in the target gas, and sufficiently permeable to an extent that allows testing to be carried out, may be used as the base substrate. In the context of this invention, an inert material refers to any material which is not reactive towards water vapour or oxygen which is present in the target gas. This material can have any suitable gas permeability, e.g. a porous material or a low permeability material. One suitable class of materials which can be used to support the sensor and can exhibit a wide range of gas barrier properties are polymers.

Polymers which are contemplated for use in the base substrate in the present invention include both organic and inorganic polymers. Examples of organic polymers which are suitable for forming the base substrate include both high and low permeability polymers such as cellophane, poly(1-trimethylsilyl-1-propyne, poly(4-methyl-2-pentyne), polyimide, polycarbonate, polyethylene, polyethersulfone, epoxy resins, polyethylene terepthalate, polystyrene, polyurethane, polyacrylate, and polydimethylphenylene oxide. Microporous and macroporous polymers such as styrene-divinylbenzene copolymers, polyvinylidene fluoride (PVDF), nylon, nitrocellulose, cellulose and acetate may also be used. Examples of inorganic polymers which are suitable in the present invention include silica (glass), nano-clays, silicones, polydimethylsiloxanes, biscyclopentadienyl iron, polyphosphazenes and derivatives thereof. The base substrate may also comprise a mixture or a combination of organic and/or inorganic polymers. These polymers can be transparent, semi transparent or completely opaque. If optical measurements on the sensing element are to be carried out in conjunction with the electrical measurement as described hereinafter, it is preferable to use a base substrate material that also provides a suitable level of reflectivity to aid in the observation or photographing of the sensing element.

As the base substrate may possess some degree of resistance to gas flow and would thus have an impact on gas permeation readings, gas permeation properties of the base substrate should preferably be characterised prior to use, so that the final measurements can be appropriately adjusted to take into account the effect of the base substrate. Where a low gas permeability material is used as the base substrate, the target gas may take a longer time to permeate through the base substrate and thus requires a longer test duration. Alternatively, if highly permeable materials, e.g. cellophane, are used as the base substrate, there will be relatively less resistance to gas flow.

In a further embodiment, the base substrate further comprises a barrier layer. In this context, a barrier layer is generally known in the art to be made from one or more layers of materials such as barrier polymers, metals or ceramics that can be used to separate a system or an article, e.g. an electronic component or food, from an environment (cf. U.S. Pat. No. 6,567,753—col. 1, line 17 to 21 or claim 5). When the base substrate comprises such a barrier layer (which preferably has a low permeability towards the target gas), the base substrate and the barrier layer each provides different types of functions in the sensor. For example, the base substrate itself may function only as a supporting structure without providing much resistance to the target gas, while the barrier layer provides the desired level of gas resistance. The respective materials chosen for the barrier layer and base substrate should each have a correspondingly suitable level of gas permeability necessary for the use of the sensor of the invention.

It is contemplated that the barrier layer can be arranged or positioned in several ways in this embodiment. In one example, the barrier layer may be present as a single layer or as a laminated sheet or coating between the sensing element and the base substrate. Alternatively, the barrier layer can be a layer located within the base substrate. It is also further contemplated that the barrier layer can be located at the bottom of the base substrate, i.e. diametrically opposed to the sensing element. Typically, if a barrier layer is present, it consists or comprises the material to be tested, i.e. the permeability of which towards a target gas is to be measured.

In another embodiment, the base substrate consists solely of the barrier layer, meaning that the sensing element is formed directly onto only a barrier layer. This embodiment provides for a means to test the permeation characteristics of the barrier layer using the sensor of the present invention. In this manner, the present embodiment can also serve for example, as a ready-made unit for use in kits to simulate the permeation processes through the barrier layer.

Suitable materials for forming the barrier layer can comprise inorganic or organic materials. Inorganic materials that are particularly suitable include metals (e.g. aluminium, iron, tin), metal oxides (e.g. $Al_2O_3$, $MgO$, $TiO_2$), ceramic oxides, inorganic polymers, organic polymers and mixtures and combinations thereof. Examples of respective inorganic polymers include organic-inorganic polymers, metal chelate coordination polymers, and completely nitrogen based inorganic polymers. Specific examples are glass, silicones, polydimethylsiloxanes, biscyclopentadienyl iron, polydichlorophosphazene and derivatives thereof, for example. Suitable organic materials include organic polymers such as acrylic-based polymers, polyimide, epoxy resins, polyalkylenes derivatives such as crosslinked polyethylene, polyethylene terephthalate, polystyrenes, polyurethanes, polyacrylates, polycarbonates, and polyethersulfones. Particularly suitable organic polymers having a suitable level of permeability and stability include PET, polycarbonate and polyethersulfone. The barrier layer can be a single layer film or a multi-layer stack. In the case of a multi-layer film where independent layers of inorganic (e.g. metal oxide) and organic materials are present, organic layers can be arranged to be sandwiched between the inorganic metal oxide films in order to provide maximum contact between the inorganic layers. Specific examples of multilayer barrier layers/stacks includes, for example, polycarbonate-aluminium oxide, PET-magnesium oxide, glass-tin oxide, aluminium oxide-polyacrylate-aluminium oxide, and an aluminium oxide-silicone-aluminium oxide stack. It is thus noted that the same material(s) may be present in the base substrate and the barrier layer. In the context of the invention, the barrier layer is typically the structure to be tested for its permeation properties using a sensor of the present invention. An example of a possible structure in which the same material(s) is present in both base substrate and barrier layer is as follows. A sensor in which a base substrate of known permeability is used has a thin layer of low gas permeability polymer e.g. polycarbonate, incorporated into the base substrate to improve the shelf life of the sensor, for example. Subsequently, when such a sensor is used for measuring the permeation properties of a test specimen, it will be attached directly onto a surface of the test specimen. For instance, the test can be carried out on a barrier layer, e.g. a composite liquid crystal display (LCD) barrier stack, which may comprise the same low gas permeability polymer that is present in the base substrate e.g. polycarbonate. In such a case, both the base substrate and the barrier layer would have polycarbonate as a common material. In another example, the base substrate may comprise polyimide films, while the barrier layer may comprise polyimide film containing silica particles/nanoclays, normally known as intercalated or exfoliated hybrids, or nano-composites. Typical examples of a nano-clay includes any member of the smectite group of clay minerals, such as montmorillonites, The electrodes of a sensor of the invention may be fabricated as wires or strips made from metals such as copper or tin, each electrodes having one end attached to the sensing element and the other end freely movable. However, where the electrodes are designed as films, it is desirable not to leave the electrodes freely movable, even though it is possible to do so, but to immobilise them directly onto the base substrate or test specimen (where the barrier layer is the test specimen). Since a film layer may be fragile and may be easily damaged, having it immobilised can help to reduce the possibility of mechanical damage. Accordingly, one embodiment of the invention is directed to the sensor in which the electrodes are formed on a surface of the base substrate.

Where the electrodes are formed on (a surface of) the base substrate, the present sensor can assume a variety of configurations. In one embodiment, the electrodes are spaced apart to form a trench. In this context, the trench is usually formed by the portion between the two electrodes, the edges of the trench being defined by the edge of each electrodes and the base of the trench being the base substrate. The components of the sensor can be arranged in several possible ways. For example, the sensing element may be placed over the trench, underneath it, or along the sides of the trench, as long as the sensing element forms an electrical connection between the two electrodes.

In one embodiment, the sensing element is located in the trench. The electrodes can be first formed to define the structure of the trench. Subsequently, when the sensing element is deposited in the trench, it is allowed to conform to the predefined dimensions of the trench, thereby allowing the sensing element to be shaped and sized. In this manner, the trench is analogous to being a mold or cast for the sensing element.

In this respect, depending on the required dimensions of the sensing element, the trench may be filled either partially or fully by the sensing element. Alternatively, the sensing element may extend outside of the trench to overlap partially the edges of the adjacent electrodes. The cross-section of the trench can typically be of a rectangular shape, square shape or any other suitable shape, as long as a suitable electrical contact is formed between the sensing element and the electrodes. For example, in one embodiment, if it is required to form a trench in which the base of the trench is narrower than the top, the electrodes may be formed with ends that taper off towards the trench. When the sensing element is subsequently deposited into the trench, a sensor with the configuration shown in FIG. 2C may be obtained. Alternatively, in another embodiment, if it is desired to form a sensing element which has a wider base than the top surface, the sensing element can first be deposited on the base substrate, and then the electrodes are deposited to overlap partially with the edges of the sensing element (cf. FIG. 2D). In both embodiments, the sensor is designed such that the plane of contact between the sensing element and an electrode is sloped, i.e. having an angle of either more or less than 90° with respect to the surface of the electrodes. Such a design improves the electrical contact between the sensing element and the electrodes, thus reducing electrical resistance at the sensor/electrodes interfaces and resulting in improved electrical conduction.

In another embodiment, the sensor comprises an encapsulation enclosing the sensing element. An encapsulation can provide for a hermetical seal around the sensor, such that the target gas is only allowed to permeate through the test specimen. Furthermore, an encapsulation would prevent the sensing element from coming into contact with ambient water vapour and oxygen prior to its use in tests. In addition, the encapsulation also acts as a protective covering which buffers any physical impact that might damage the sensing element.

The material for forming the encapsulation material, meaning the encapsulant, may comprise any type of material which is preferably substantially low gas permeability. Many types of polymers may be used for this purpose, including hydrocarbon plastics, thermoplastics, rubbers and inorganic polymers. Examples of suitable organic polymers are ultraviolet (UV) curable epoxies, polysulfides, silicone, polyurethane, polystyrene, polyalkylenes, polyimides, polybenzoxazoles and polyacrylates. If it is required to provide an encapsulation that is able to conform fully to the shape of the sensor, suitable materials are preferably available as a mouldable gel or viscous fluid which can subsequently be cured and hardened by heat or UV radiation.

The encapsulation can assume a variety of configurations. One contemplated configuration is to have the encapsulation cast as a hard covering around the exposed surfaces of the sensor. The encapsulation may be in direct contact with the sensing element, or it can surround the sensing element without being in direct contact with the sensing element. In the former case, the sensing element is enclosed entirely within the encapsulation, so that the present sensor can be used to simulate the encapsulating structure of light emitting diodes (LED). In the latter case, the encapsulation can provide a hollow space around the sensing element. The hollow space can be filled with an inert gas, such as nitrogen or one of the noble gases such as argon.

In another embodiment, the sensor further comprises a cover substrate, wherein the encapsulation forms side (lateral) walls surrounding the sensing element, and the cover substrate is arranged to be in contact with the side (lateral) walls. In more detail, in this embodiment, the encapsulation is applied onto the base substrate/test specimen around the perimeter of the sensing element, thereby encircling the sensing element, while the cover substrate is placed onto the side (lateral) wall like a lid. Such an arrangement constitutes the encapsulating structure housing the sensing element. Furthermore, the cover substrate may be placed on the side walls in an inert gas environment, so that inert gas can be trapped within the encapsulating structure. In this respect, the encapsulant that is used can be a UV (ultraviolet) curable epoxy or any other suitable sealant. This embodiment provides a means to simulate and thus assess the gas permeability of multi-layer organic/inorganic thin films and encapsulating structures, such as those found in organic light emitting devices (OLED) and FOLEDs. The gas permeability in turn allows an estimation of the lifespan of the oxygen or moisture sensitive device within the encapsulating structure. Essentially, the sensor is structured analogously to the encapsulating structure. For example, to carry out a simulation of gas permeation in the encapsulating structure of an OLED under ambient conditions, the same OLED device can fabricated (cf. FIGS. 7A and 7B) with the light emitting device replaced by a sensing element of the present invention.

In general, materials that are used for forming the cover substrate should preferably have low gas permeability in order to provide a good hermetical seal for the sensor. The base and cover substrate can comprise any material such as polymers, barrier coated polymer, glass, aluminium foil. Examples of materials comprising the base or cover substrate are glass, low gas permeability polymers and metal laminated foils. For reasons of cost, glass, aluminium and copper are preferred in some embodiments.

As can be seen from the above, the present sensor is sufficiently versatile to be used for the determination of gas permeability in a wide variety of applications, including the gas permeability of polymer substrates, encapsulants, sealants, adhesives as well as overall encapsulating structures.

In one embodiment, the sensor further comprises a protective layer covering at least a portion of the sensing element. The purpose of the protective layer is to prevent any contamination or premature degradation of the sensing element. This can arise due to defects in the encapsulating structure housing the sensing element. By covering exposed surfaces of the sensing element with a protective layer, the opportunity for any reactive gas to come into contact with the sensing element can be reduced. If it is desired to improve the protection of the sensing element, the protective layer can also comprise an electrically insulating material. For this purpose, the protective layer can be formed using any organic or inorganic material. Suitable materials include metal oxides, metal fluorides, organic polymers and a mixture thereof. Examples of particularly suitable materials include, but are not limited to metal oxides such as aluminium oxide, calcium oxide, magnesium oxide, and metal fluorides such as sodium fluoride, lithium fluoride and magnesium fluoride. In addition to the above materials, other suitable materials include metals and metal alloys. Particularly suitable metals and alloys include, but are not limited to copper, silver, platinum, gold and mixtures thereof. If the protective layer comprises a metal or alloy, the metal or alloy should preferably not come into direct contact with the sensing element. This helps to ensure that the bulk electrical properties of the sensor are not influenced by a further electrical component connected to it, thus allowing more precise measurements of the bulk electrical properties of this embodiment of the sensor to be obtained. Consequently, if an electrically conductive material such as a metal or alloy is used in the protective layer, it may be advantageous to position an electrically insulating layer, comprising for instance any one of the aforesaid metal oxides or metal fluorides, between the conductive layer and the sensing element. Accordingly, the term 'protective layer' may denote not only a single layer, but it may also denote 2 or more layers, i.e. a multi-layer arrangement.

In another embodiment of the invention, the sensor further comprises an liner layer (comprising or consisting of organic and/or inorganic polymers) interposed between the sensor and the base substrate. Materials such as inorganic coatings or layers (e.g. a metal oxide coating) may have or develop amorphous zones or defects in the form of pinholes, cracks, or grain boundaries. When such defects are present in the surface of the barrier coating covering the polymer substrate, the permeating gases can escape through the defects at a higher rate than at other locations on the surface of the sample where there are no defects. Consequently, a portion of the sensing element that is adjacent to such defects will be reacted at a higher rate. The non-uniform degradation of the sensing element may leave sections of unreacted material within the sensing element, thereby resulting in an inaccurate reading. The liner layer usually behaves as a buffer region which sponges up (saturate with) the permeating gases before they are desorbed homogeneously. The homogeneous desorption of the permeating gases results in the uniform degradation of the sensing element, which in turn enables the decrease in electrical conductivity of the sensor to be more accurately correlated to the decrease in thickness of the sensing element.

It is noted that the liner layer is not necessary, when the test material comprises or consists of plain organic polymers, defect free metals, or low gas permeability polymers having an organic top layer where a multi-layer barrier layer is used. In general, test materials that do not suffer from surface defects do not require the use of an liner layer. However, a liner layer can be applied if it is desired to improve the performance of the sensor.

The liner layer can be deposited as a layer having thickness ranging from 10 nm up to a few microns or higher. It can comprise any organic material that exhibits relatively little gas barrier properties may be used. Examples of suitable materials include organic polymers such as polyvinyl alcohol, polyethylene oxide, polyvinyl pyrrolidone, as well as copolymers thereof, Other suitable polymers include parylene type polymers, and acrylic polymers such as polyacrylates (e.g. poly methyl methacrylate), polyacrylic acids, and polyacrylamides. Cellophane films are also suitable for use in or as an organic liner layer. Furthermore, the liner layer can also comprise a combination of inorganic polymers such as silicone-type polymers, polysilanes, polygermanes, polystannanes and polyphosphazenes. It is noted in this conjunction that some of the materials specified for the base substrate (layer) and barrier layer are also common to the liner layer, meaning that it is possible that the same material is selected for the base substrate, barrier layer and/or liner layer. For example, if the base substrate comprises a particular polymer, the liner layer can also comprise the same polymer. In another example, if the base substrate is a polymer or a composite comprising inorganic materials such as silicon oxide or other oxides including nano-clays or particles, the barrier layer also may likewise comprise the same polymer or composite materials.

In another aspect, the invention relates to a method of producing a sensor for measuring the gas permeability of a test material as described above, said method comprising providing two electrodes, and connecting an electrically conductive sensing element that comprises a water and/or oxygen sensitive material to said two electrodes.

Both the sensing element and electrodes can be obtained as prefabricated items with a specific form e.g. a wafers, strips or desiccant pads, which can be assembled directly to form the sensor. Alternatively, if the sensing is to be formed as a film on the surface of a test specimen via film deposition methods, e.g. thermal evaporation or sputtering or any surface technology, the sensing element can be procured in a form that is suitable for use in film deposition equipment and then subsequently shaped and molded into a desired form to form the sensor.

For the purpose of carrying out the present method, the electrodes can be provided for fabrication of the sensor in several ways. For example, it is possible to first suspend the electrodes on a pair of holders and then solder the sensing element to the electrodes. Alternatively, in one embodiment, the sensing element is immobilised on a support, e.g. on a surface of a base substrate, and thereafter the electrodes are soldered to the sensing element. The skilled person will appreciate that it is not always necessary to solder the sensing element and the electrodes to form a functional electrical connection. It may be sufficient to form the sensing element directly onto the electrodes, or vice versa, and to secure the arrangement by means of a weight placed thereupon, without having to connect them via soldering, conductive adhesives or other connection means. However, depending on the application and the type of electrode and sensor utilised, any suitable type of connection means may be used.

In another embodiment of the present method, the electrodes are formed on a surface of a base substrate (which can be the material to be tested). Where the electrodes are electrical wires, the electrodes may first be immobilised on the substrate with the contact areas exposed, leaving a gap between the electrodes that corresponds to the location of the sensing element, and then forming the sensing element in the gap contacting the electrodes. Where the electrodes are to be formed as thin or thick films, conventional film deposition techniques such as vacuum vapour deposition (VVD), physical vapour deposition (PVD), chemical vapour deposition (CVD), thermal evaporation, sputtering, or any other surface deposition technology may be used. The material for the sensing element may then be evaporated into the gap formed between the electrodes using a suitable mask, or conventional lithography or etching techniques, or any thermal evaporation techniques such as those described for forming the electrodes.

The present method can be carried out according to any suitable sequence of steps. For example, the electrodes can first be formed on the test material before depositing the sensing element. Alternatively, it is also possible to first form the sensing element onto the test material before forming the connecting electrodes.

When measurements requiring high levels of sensitivity (e.g. lower than $10^{-3}$ g/m$^2$/day) are to be carried out with a sensor of the invention, tests on low gas permeability materials should ideally be performed with test materials and sensor components that are substantially devoid of contaminants, such as oxygen and water reactive substances or macro scale adsorbed particles found on their surfaces. For this reason, it is desirable (though not necessary) that the sensor components as well as the test material are cleaned to remove any contaminant, including macro scale adsorbed particles, which may be introduced during the course of manufacturing, or when carrying out the deposition processes. Any combination of conventional surface cleaning techniques commonly used in the semiconductor industry may be used, such as laser cleaning, physical and chemical plasma processes, UV radiation and silicon flux.

In one embodiment of the method of producing a sensor of invention, the surface of the test material is subjected to a surface preparation procedure in order to remove such contaminants. One preferred surface preparation procedure comprises rinsing the test material or substrate and its deposited electrode with an alcohol, blow-drying with an inert gas, and vacuum degassing. Suitable alcohols which may be used includes secondary, tertiary, and branched-chain alcohols, e.g. iso-propyl alcohol or iso-butyl alcohol. In practice, the skilled person will appreciate that cleaning with chemicals such as acetone and/or short-chain primary alcohols such as methanol or any other chemical that can act as an organic solvent towards any polymer in the substrate, may not be suitable in certain embodiments in the method of preparing a sensor of the invention. Accordingly, if a polymer that is not resistant to such chemicals is present in the base substrate and/or liner layer, these chemicals may not be used in the cleaning procedure. Nevertheless, if all polymers or other materials present in the base substrate are resistant to these chemicals, they may then be used for cleaning.

In the above surface preparation procedure, after the sensor is rinsed with alcohol, it is blow-dried using high pressure gas to get rid of traces of the rinsing alcohol. Subsequently, the sensor is placed in a vacuum oven in order to ensure that the surface is free of adsorbed moisture or oxygen. In cases where organic polymers are used in the sensor, the temperature at which vacuum degassing may be carried out may then depend on the organic polymer used and the respective glass transition temperature(s). In general, suitable temperatures for carrying out vacuum degassing are below the glass transition temperature ($T_g$) of the polymer(s) present in the base substrate. For example, where conventional LCD barrier stacks are used, vacuum degassing may be carried out at temperatures of between 30° C. to 100° C., preferably between 50° C. to 85° C., and under partial pressure for 1 to 80 hours, preferably 6 to 60 hours.

In a further embodiment, the surface on which the sensor is formed is treated with argon gas plasma after vacuum degassing. Prior to forming the sensing element, RF argon plasma may be used to bombard the surface of the barrier film with low energy ions in order to remove trace amounts of surface contaminants. Depending on the surface condition, plasma treatment can be carried out using plasma power of 30 W to 2 kW, using argon gas flow of 20 sccm to 100 sccm and a duration of 10 s to 2 hr. For example, when indium tin oxide (ITO) is used as a barrier layer, a suitable plasma treatment comprises RF power of 200 W, substrate bias 50V, argon gas of 70 sccm and treatment duration of 5 to 8 eight minutes.

In order to decrease the chances of any unwanted degradation of the sensing element, the exposed surfaces of the sensing element can be protected from exposure to water vapour or oxygen by applying a protective and preferably insulating layer thereon, after the deposition of the sensing element has been carried out. The insulating layer can comprise any type of organic or inorganic layer, such as a thin film deposited by conventional processes e.g. PVD or CVD. Transparent films such as lithium fluoride and magnesium fluoride are suitable for this purpose.

After carrying out the plasma treatment process, a liner or buffer layer can be formed if the test substrate comprises an inorganic (e.g. metal or metal oxide) layer as a terminating or top layer. The liner layer can be deposited as a thin layer by spin coating or vacuum evaporation or any other conventional surface deposition process.

Another embodiment of the present method further comprises encapsulating the sensing element. Conventional encapsulation techniques for encapsulating the sensing element may be used and may be carried out in an inert environment, such as a glove box. For example, transfer molding, which involves placing the sensing element into a cavity of a mold and then injecting a thermosetting material into the cavity, may be carried out in order to form the sensor. The thermosetting material is allowed to flow over the sensing element until it is covered entirely, and is thereafter cured so that it hardens into a protective covering. When the sensor includes a substrate, the sensing element and at least a portion of the substrate may be placed into the mold cavity. The thermosetting material can be made to flow over the whole sensing element on one side of the substrate, and then allowed to set. An ultraviolet (UV) curable sealant, e.g. epoxy, can be used for this purpose.

One variation to the above encapsulation procedure comprises applying the sealant to the rim of the substrate, followed by sealing the sensing element with a cover substrate, e.g. a glass cover. The cover substrate can be transparent in order to provide a view of the sensing element during the course of carrying out the performance test. However, an opaque cover may be used if it is not necessary to view or to take photographs of the sensing element as it degenerates during the course of the measurement test. As an added measure to maintain a contaminant free environment in the test chamber, the cover substrate may also be cleaned before use, for example, by rinsing it in acetone and water.

In a further aspect, the invention is also directed to a system for measuring gas permeability of a test material, said system comprising the sensor of the present invention. The system may comprise a test chamber, a constant current source, a digital signal analyser and a meter for measuring resistance.

In more detail, the test sample with its accompanying sensor may placed in a suitable chamber where the humidity, pressure and temperature can be set to any desired level in order to simulate a particular environment. If a humidity chamber is used for the test, the permeation of other gases, e.g. oxygen, through the test material may also be studied by introducing these gases into the chamber during the test. The electrodes of the sensor are connected to a constant current source meter which may in turn be interfaced with a computer that records the data transmitted from the meter at a regular interval. Any suitable constant current source meter can be used in the present system. Examples are those which are available from Keithley (Ohio, USA), Bridge Technology (Arizona, USA), or Glen Spectra (Middlesex, UK). A data plotting software may be used so that the resistance of the sensor can be plotted as a function of time.

The system further comprises a dynamic spectrum analyser to evaluate the 1/f noise of the sensor when carrying out the test. Suitable spectrum signal analysers which may be used include HP35670A, HP3561A or HP35665A from Agilent (California, USA) and SR785 or SR780 from Stanford Research (CA, USA). It is also desirable to choose an analyser that provides a fast Fourier transform (FFT) routine to evaluate spectral density of the noise signal. Optionally, a low noise amplifier, such as Stanford Research's SR570 low noise amplifier, can be used to amplify the noise signals prior to being processed by the signal analyser.

The measuring system may incorporate not only a humidity chamber but also other suitable types of test chambers in which test materials can be tested against other gases apart from water vapour and under different conditions. Examples of suitable chambers include pressurised gas chambers and hyperbaric oxygen chambers. A preferred setup of a test chamber in which gas permeation measurements can be carried out (see FIG. 13) may comprise a hollow centre portion that is partitioned by a test specimen (substrate or film) into two sections. One section is provided with a test gas at a pre-determined pressure and temperature and on the other side of the test specimen, an inert gas is provided at the same or different pressure as a sweep gas to evacuate any test gas present. Prior to mounting the test specimen into the gas chamber, a sensor is fabricated on the test specimen and attached to the side walls of the gas chamber.

Another aspect of the present invention is directed a method for determining gas permeability. This method comprises contacting the sensing element of a sensor of the present invention with water and/or oxygen during a measurement test, measuring the change in electrical conductivity of the sensor over a period of time, and calculating the gas permeability of the test material based on the measurements.

The calculation of gas permeability is based on the rate at which the sensing element reacts with the target gas. One initial value that is usually established in order to calculate the rate of reaction is the initial quantity of sensing element. For this reason, a specified quantity of material can advantageously be used for the fabrication of the sensing element. Alternatively, the sensing element can be designed to have a pre-determined dimension (length×breadth×height), from which the quantity of sensing element can be calculated using the formula (I):

$$\text{Amount of sensing element reacted (mol)} = \frac{\text{Volume} \times \text{Density}}{A_r},$$

wherein the variable "Volume" refers to the volume of the sensing element, "Density" refers to the density of the sensing element, and "$A_r$" refers to the relative atomic mass of the sensing element. By multiplying the (molar) quantity of sensing element used in the sensor by the stoichiometric amount of reacting of water or oxygen or any other gas, the quantity of gas which reacts with the sensing element can be obtained. This quantity is taken to be equivalent to the quantity of gas transmitted through the test specimen or test structure.

The amount of time taken for the sensor to cease conducting electricity partially or fully, i.e. the measured electrical conductivity=0 Mho, is also usually needed, and can be determined with a source meter. Gas transmission rate can be calculated from the formula (II):

Gas transmission rate=Quantity of water transmitted per unit surface area (g)×(24 hr/Time)

where the variable "Time" refers to the time taken for the sensor to cease conducting. In this respect, it is noted that it may be useful to calibrate the sensor by determining the time needed for the entire consumption/reaction of a specific amount/configuration of sensing element. Once such a calibration is done, a reference point is obtained which the subsequent use of a sensor with a sensing element having the same dimensions and characteristics can rely upon. In such a subsequent use, the calibrated sensor may then require only a partial reaction of the sensing element.

Instead of calculating gas transmission based on the reacted amount of sensing element, it is also possible to calculate gas transmission based on other variables such as electrical resistance or conductivity of the sensing element, for instance. In one embodiment, the measurement of 1/f noise of the sensor is carried out to determine the gas permeability. A brief introduction to 1/f noise in the context of this invention is as follows. It is known that signals such as a current flowing through a resistor, the resistance of the resistor, or the voltage across the resistor, exhibit random fluctuations. These fluctuations, termed the noise of the signal, are characteristic of the signal. The power spectra of the noise P(f) as a function of the frequency f generally behaves according to the equation: $P(f)=1/f^\beta$. Where $\beta=1$ or $\beta$ is close to 1, the type of noise exhibited is normally referred to simply as 1/f noise (or pink noise) which occurs very often in processes found in nature (for example the 1/f noise is seen in any molecular movement or electron movement). If $\beta=0$, it is normally called white noise. If $\beta=2$, it is called brown noise. The power spectra P(f) of all noise forms such as 1/f noise, white noise, brown noise and other type of noise can all be measured with a dynamic spectrum analyser. In determining the 1/f noise of a signal as a function of another measurable variable that changes during the course of the measurement test, such as electrical resistance, the following calculation method may be taken. Firstly, the fluctuation of the signal with respect to a mean value over a period of time is recorded as fluctuation data. This mean value can for instance be the average value of the signal over that period of time. Subsequently, the fluctuation data is Fourier-transformed from the time domain into the frequency domain. Finally, the probability of fluctuation (also known as the spectral density of the signal) is plotted as a function of the other variable, such as electrical resistance as mentioned above. Such a plot typically shows that the change in spectral density is proportional to the change in the variable. In this way, measurements of 1/f noise can be directly correlated to changes in the variable.

This embodiment relies on the relationship between the change in 1/f noise (dN) and the change in resistance of the sensor (dR). In order to determine this relationship, a digital signal analyser can be used directly to evaluate 1/f noise as a function of sensor resistance as the test progresses. The measurement of resistance of the sensor is simultaneously carried out with the measurement of 1/f noise during the test. A computer interfaced with the system can be programmed to tabulate and graph N vs R, and thus obtain the rate of change of 1/f noise with respect to resistance (dN/dR).

Experimental variables and initial values that are usually established for the calculation of gas permeability in the embodiment using the 1/f noise include the initial thickness of the sensing element, initial sensor resistance, conductance, time taken for the test, and the sensitivity of the digital signal analyser's 1/f noise analysis (S).

The following general formulas show the calculations that need to be carried out to obtain gas transmission rate based on (dN/dR):

Change in resistance per unit change in 1/f noise
$(R_{1/f})=S\div(dN/dR)$ (III)

Change in sensor thickness=$R_{1/f}$×(sensing element thickness÷initial sensor resistance) (IV)

Once the change in sensor thickness has been determined, gas transmission rate can be readily calculated using Formula (I) and (II).

One advantage in monitoring the change in 1/f noise instead of measuring directly the change in the variable to be measured can be attributed to the high sensitivity level of sensitivity provided by digital signal analysers in reading 1/f noise (typically less than $1\times10^{-14}$ $V^2_{rms}$/Hz). This level of sensitivity can be about 5 to 7 orders of magnitude smaller than the value of the 1/f noise that is being measured. This facilitates the detection of very fine oxidation in the sensor and therefore enables the measurement of gas transmission rates of less than $10^{-8}$ g/m²/day. For example, the change in 1/f noise of the sensor can be measured and plotted as a function of sensor resistance. From the plotted graph, it will be seen that dN/dR is very small, meaning that the measurable unit change in 1/f noise corresponds to very small unit change of about $10^{-7}$ to $10^{-8}$ ohms in resistance. This translates into a sensitivity for detecting water vapour transmission rate of about $10^{-8}$ g/m²/day and oxygen transport rates of $10^{-8}$ cc/m²/day at temperatures of between 20° C. to 95° C. This level of sensitivity is sufficient for the purposes of testing low gas permeability materials and structures such as that found in FOLEDs.

In addition to improved sensitivity, the present invention has the advantage in being able to determine diffusion coefficient, permeability coefficient as well as the solubility coefficient of a test material using a single test, whereas previously it was only possible to determine ach of these coefficients by carrying out separate independent tests.

From the foregoing description, it can be seen that the invention can be applied to many types of applications including, for example, the testing of flexible and rigid polymer substrates having either single or multiple protective layers, encapsulation structures with or without cover substrates, epoxy or adhesive materials or taps on the rim or polymer substrate, substrates with barrier/protective layer comprising multi-layer organic or inorganic thin films. This multi-layer can have several ceramic oxide layers or inorganic layers and organic layers to provide low gas permeability performance encapsulation. Such applications are widely employed in electronics packaging applications, such as display panels using hermetically sealed OLED devices, liquid crystal displays (LCD) and integrated chip packages/structures. The material which are used for forming these substrates include polymers such as polyethylene, polyethylene sulphide, polycarbonate, substrates which can be laminated with a single or multiple layers of metal oxide or ceramic barrier coatings, as well as glass substrates. Other applications in which the present invention may be used are the measurement of gas permeation properties of LEDs, OLED, and LCD encapsulation, hard disk drive metallic enclosures, as well as food and drug packages, vacuum applications, ammunition containers, and plastic containers.

The invention will be further explained by the following non-limiting examples and the accompanying figures, in which:

FIG. 6 shows a sensor that is configured in an analogous manner to a conventional OLED device.

FIGS. 7A and 7B show two different types of OLED encapsulation structures.

Figure 10A:
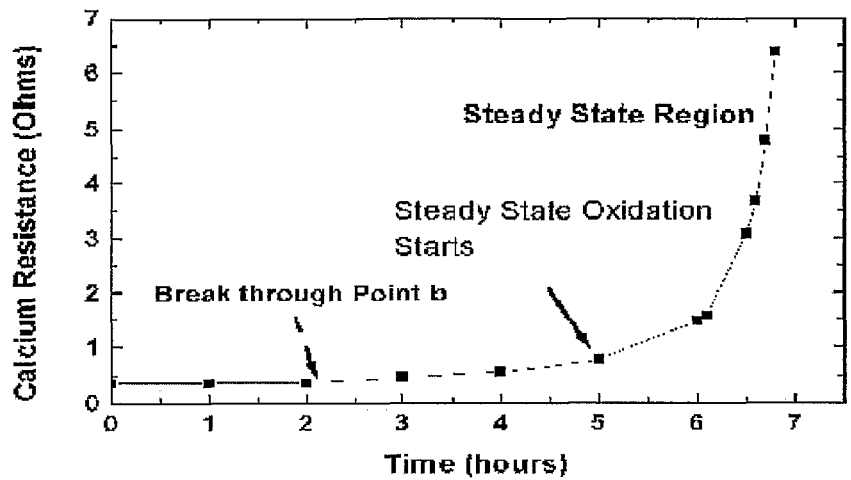
Figure 10B:
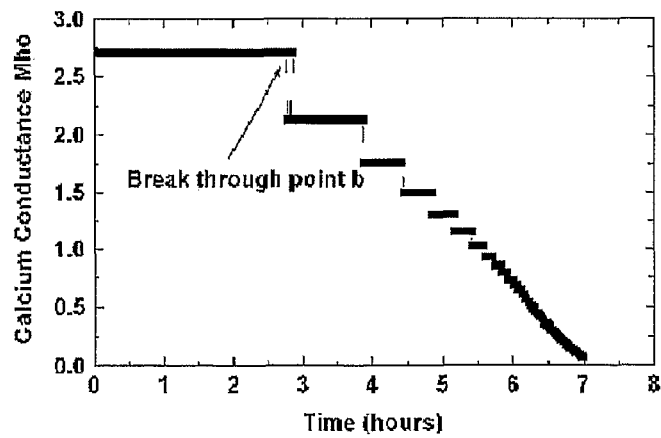
Figure 10C:
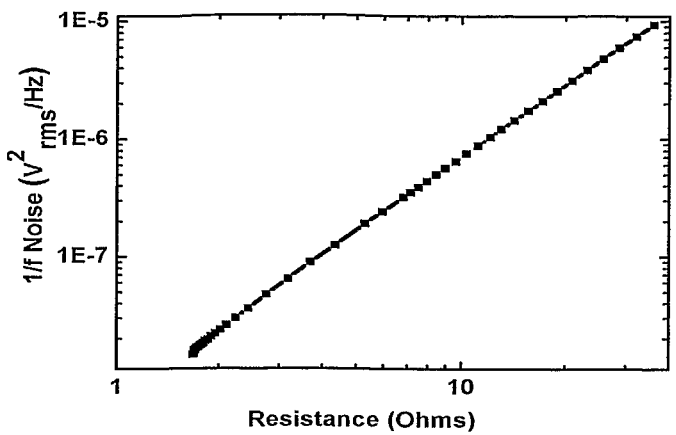

FIGS. 10A to 10C show the measurements obtained in a test where commercial substrates were coated with silicon dioxide coating. FIG. 10A shows the graph of 'Calcium Resistance vs. Time'; FIG. 10B shows the graph of 'Calcium Conductance vs. Time'; FIG. 10C shows a graph of '1/f noise of the sensor vs. Resistance of the sensor'.

Figure 11A:
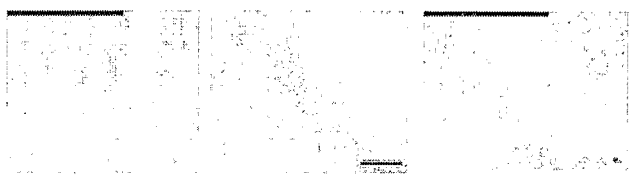
Figure 11B:
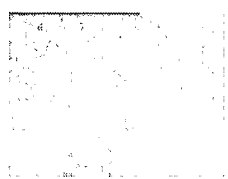

FIGS. 11A and 11B are digital images of a calcium sensing element used in a test on a polyethylene terephthalate (PET) substrate. FIG. 11A shows the images of the calcium sensing element taken at different time intervals at 10× magnification. FIG. 11B shows the image of the calcium sensing element in a control setup.

Figure 12A:
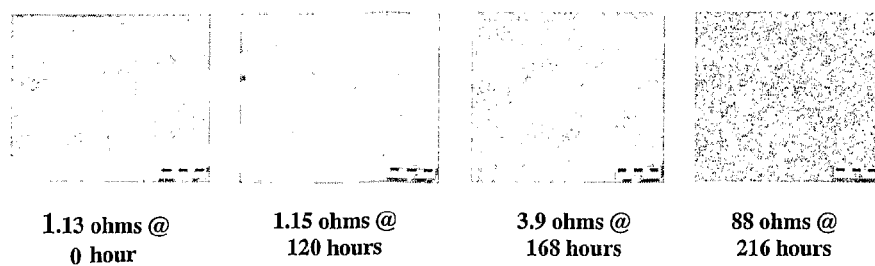
Figure 12B:
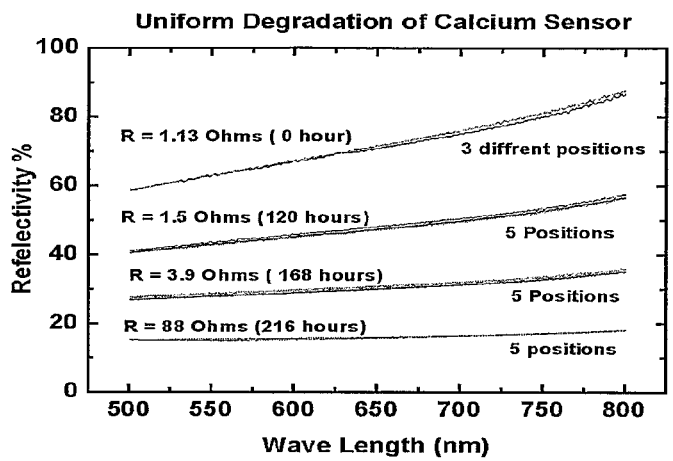

FIGS. 12A and 12B are digital images of a calcium sensing element used in a test on a glass substrate. FIG. 12A shows the degradation pattern of the sensor at different time intervals. FIG. 12B shows the reflectance of the calcium sensing element at different time intervals.

Figure 13:
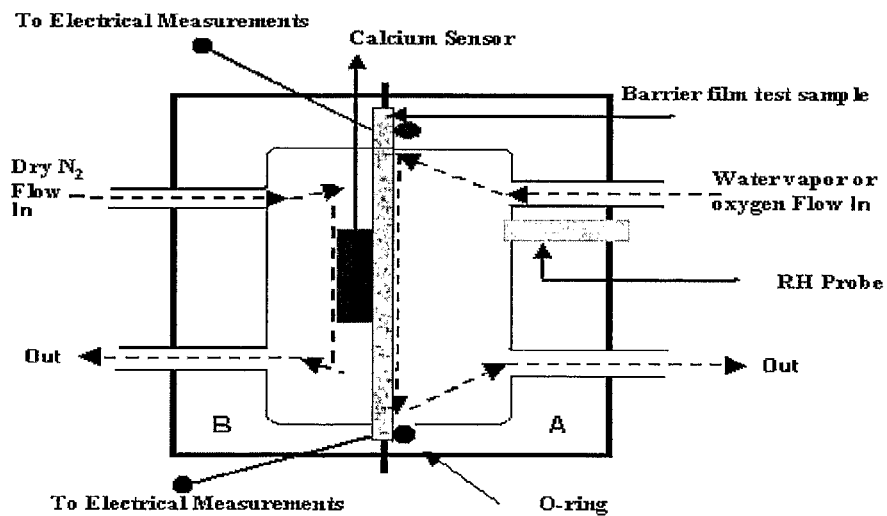

FIG. 13 shows a gas permeation test cell which can be used to carry out permeation tests with a sensor of the invention.

EXAMPLE 1

Exemplary Embodiments of a Sensor of the Invention

Exemplary Embodiment 1

Figure 1:
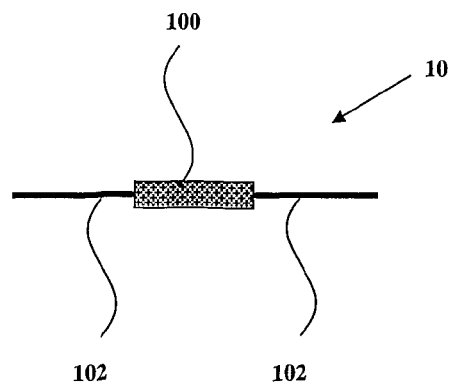
FIG. 1 shows a sectional view of one embodiment of a sensor of the present invention.

FIG. 1 depicts a sensor 10 according to the invention, in which a sensing element 100, such as a strip of calcium, is connected to a pair of electrodes 102. It can be seen from the figure that the electrodes 102 are connected to the short edge of the sensor. A contact adhesive such as bond pads may be applied over the short edge of the sensing element used to improve the contact between the electrode and the sensing element. The electrodes may be connected either at the short edge or the long edge of the sensing element.

Exemplary Embodiment 2

Figure 2A:
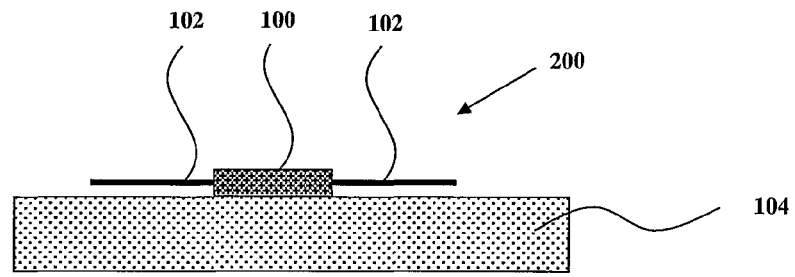
FIGS. 2A to 2F show different embodiments of the sensor supported by a base substrate.

FIGS. 2A to 2G shows various embodiments of a sensor 200 that is supported by a base substrate 104. In FIG. 2A, the electrodes 102 are held above the base substrate 104.

Figure 2B:
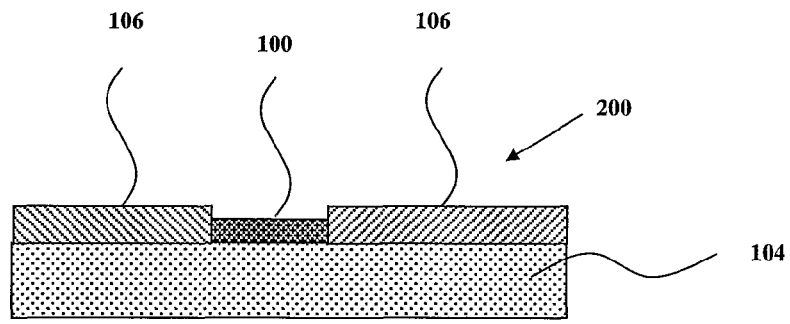
Figure 2C:
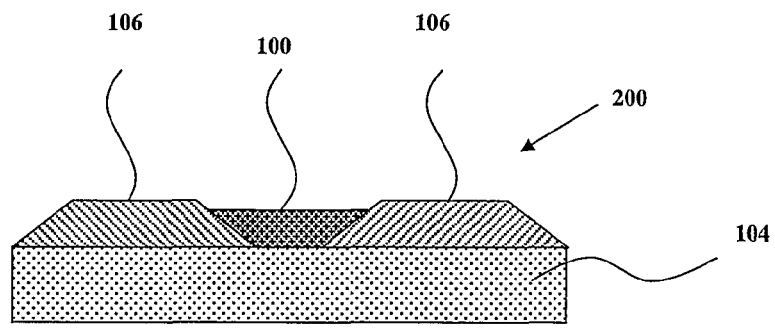

FIGS. 2B to 2G show a sensor 200 in which the electrodes 106 are located on a surface of the test material and are spaced apart to form a gap/trench in between. The trench is occupied by the sensing element 100. In FIG. 2B, the plane of contact between the electrodes and the sensing element is vertical with respect to the base substrate. In FIG. 2C, the plane of contact is not vertical to the surface of the substrate but forms an angle that is less than 90°. The cross-sectional view of the sensor shows a sensing element which has a narrow base surface and a wide top surface. This configuration can for example be formed by first forming the electrodes on a substrate, and then controlling the deposition process to form electrodes which taper off at the ends. Subsequently, the sensing element 100 is deposited between the two electrodes.

Figure 2D:
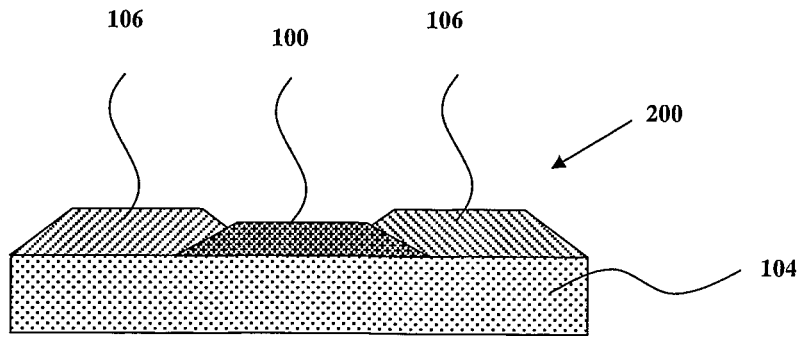
Figure 2E:
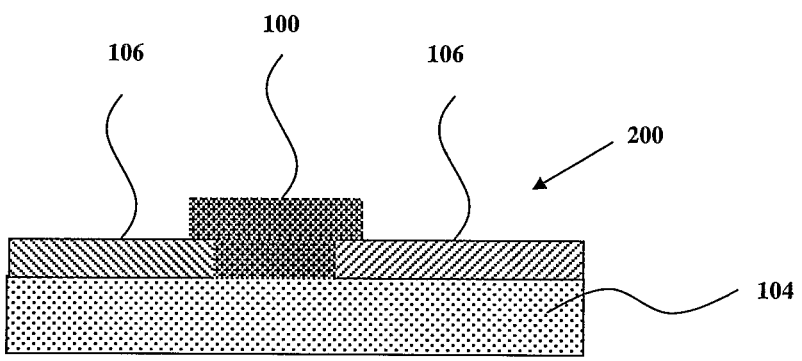
Figure 2F:
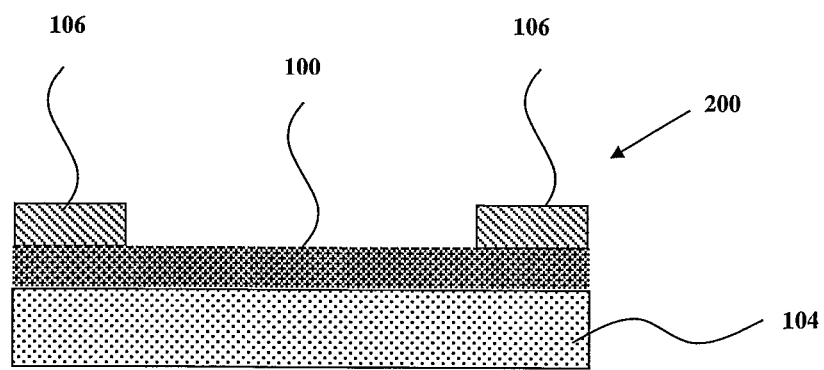
Figure 2G:
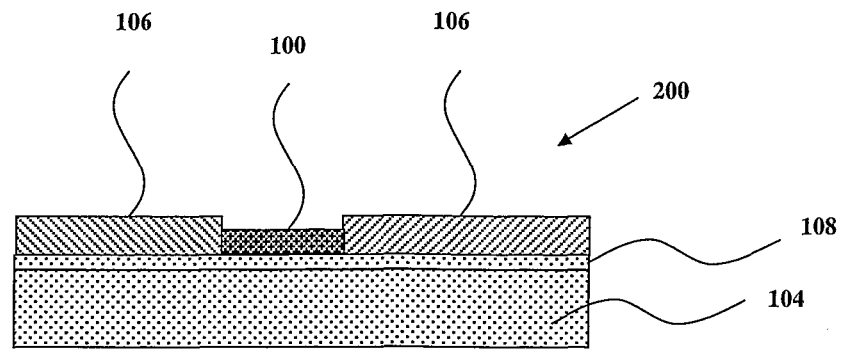
FIG. 2G shows a sensor that is supported on a barrier coated substrate.

FIG. 2D shows a sensor 200 where the sensing element 100 has a base surface which is wider than the top surface. In this example, the angle of contact between the sensing element and the electrodes is about 45°. FIG. 2E shows a sensor 200 in which the sensing element extends out of the trench between the electrodes 106 and overlaps partially with the electrodes 106. FIG. 2F shows a sensor 200 in which the sensing element extends over the surface of the substrate 104 and the electrodes 106 are formed on the sensing element. FIG. 2G shows a sensor 200 in which the substrate 104 is coated with a barrier layer 108.

Exemplary Embodiment 3

Figure 3A:
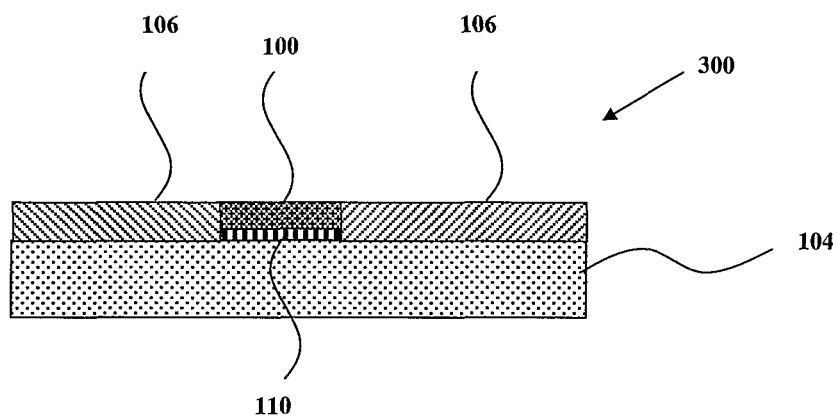
FIGS. 3A and 3B show different embodiments of a sensor of the invention incorporating a liner layer.
Figure 3B:
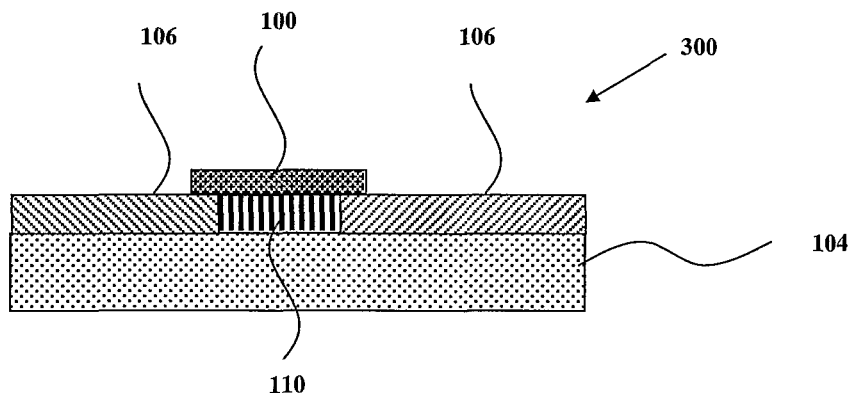

FIGS. 3A and 3B depicts embodiments of a sensor 300 which incorporates an liner layer 110 between the sensing element and the base substrate. FIG. 3A shows the liner layer to be positioned between the base substrate and the sensing element. FIG. 3B shows the liner layer to be flush with the electrodes, i.e. having about the same thickness as the electrodes.

Exemplary Embodiment 4

Figure 4A:
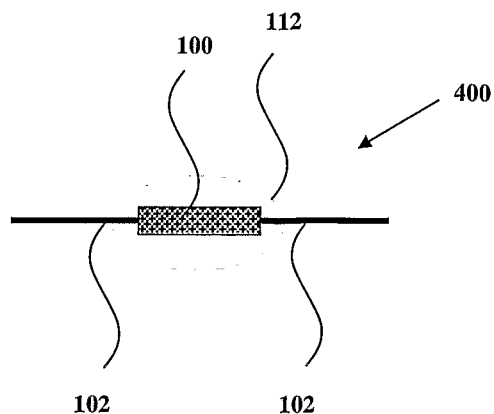
FIGS. 4A and 4B show a sensor that incorporates an encapsulation.
Figure 4B:
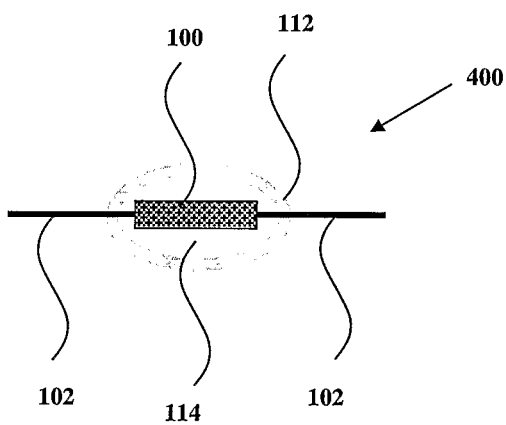

FIG. 4A shows a sensor 400 which is enclosed in an encapsulation 112. FIG. 4B shows a sensor in which the encapsulation 112 is not in direct physical contact with the sensing element 100 but provides a hollow space 114. The hollow space can be evacuated or filled with an inert gas if required. In one specific embodiment, the encapsulation 112 is an epoxy resin and hollow space 114 is filled with argon gas. In another specific embodiment, the encapsulation 112 is a polyurethane resin and the hollow space is filled with nitrogen gas.

Exemplary Embodiment 5

Figure 5:
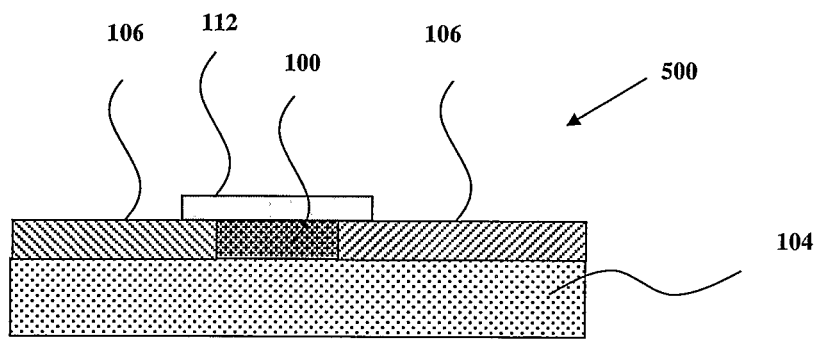
FIG. 5 shows a sensor that is formed on a base substrate and which comprises an encapsulation.

FIG. 5 shows an encapsulated sensor 500 in which the electrodes 106 are formed on a surface of a substrate 104. The electrodes 106 are spaced apart to form a trench which accommodates the sensing element 100. The thickness of the sensing element 100 is approximately level with the thickness of the electrodes 106. An encapsulation 112 is formed over the sensing element 100.

Exemplary Embodiment 6

FIG. 6 shows a sensor 600 which incorporates an encapsulation and comprises a cover substrate 114 adjacent to the encapsulation. In this embodiment, a layer of encapsulation 112 is applied on the electrodes and base substrate, around the sensing element 100. The cover substrate 114 is placed on the encapsulation 112, thereby sealing the sensing element 100. The hollow space 116 enclosed within the encapsulation and cover substrate may be filled with an inert gas such as argon or nitrogen. This configuration is suitable for testing gas permeation properties of OLED packages, which have structures shown in FIGS. 7A and 7B.

Exemplary Embodiment 7

Figure 8:
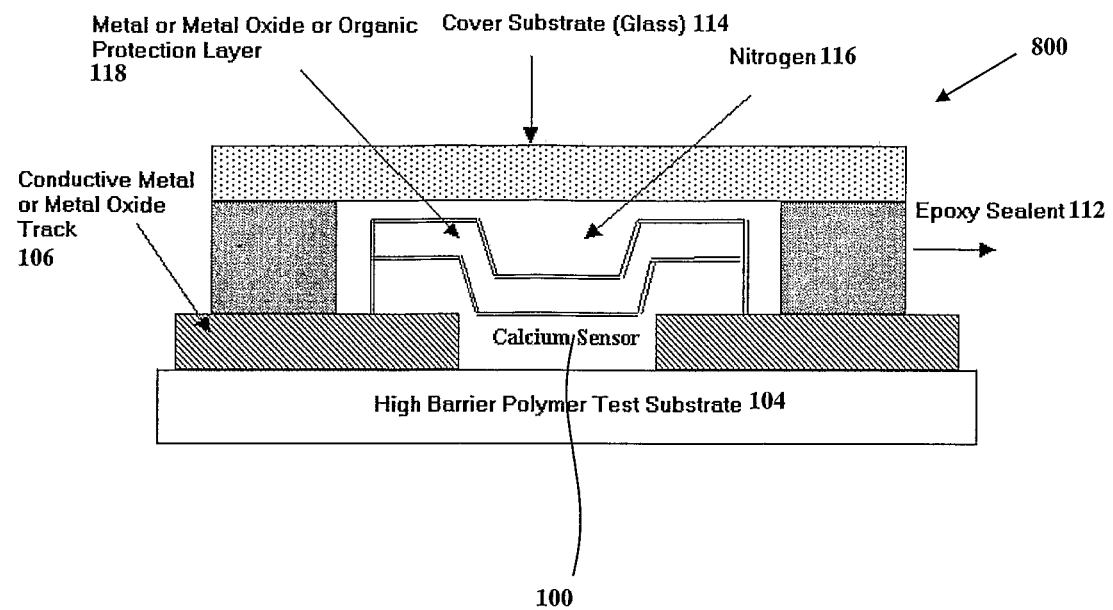
FIG. 8 depicts an encapsulated sensor that is formed on a substrate and which incorporates a protective layer formed on a surface of the sensing element.

FIG. 8 shows a sensor 800 which incorporates an encapsulation/sealant 112 comprising epoxy and a glass cover substrate 114. In this embodiment, a layer of encapsulation 112 (epoxy sealant) is applied on the test specimen 104 and the pair of metal tracks 106 constituting the electrodes. Calcium is used as sensing element 100 and the top of the sensing element 100 surface is covered with a protective layer 118. The glass cover substrate is placed on the encapsulation, thereby sealing the sensing element. The hollow space 116 enclosed above the sensing element is filled with nitrogen.

EXAMPLE 2

Fabrication of a Gas Permeability Sensor

Figure 9:
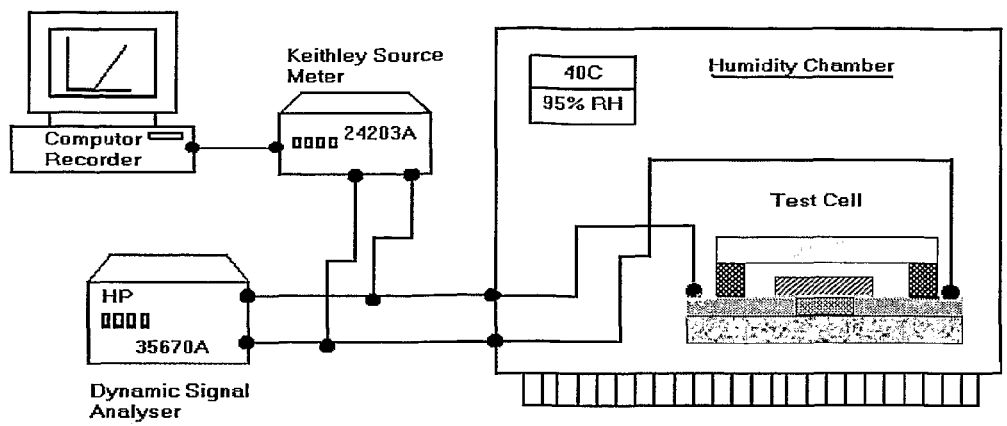
FIG. 9 depicts a schematic diagram of a measurement system.

In this example, a sensor as illustrated in FIG. 8 and as shown schematically in FIG. 9 was produced. The test sample (thickness 175 μm) comprised a 133 μm thick polycarbonate film coated with 30 nm thick silicon oxide barrier layer. The test sample (substrate) was slit into 50 mm by 50 mm dimensions with a pneumatically operated hollow die punch-cutting machine. After slitting was performed, silver was deposited onto the test sample using a suitable mask to form two electrically conductive tracks onto the test sample surface. The conductive tracks were orientated such that the width of each track faces each other. Two strips of conductive metal (silver) tracks with a thickness of 300 nm (18 mm length and 20 mm width) were deposited on the test sample, thereby forming in between them a 10 mm length×20 mm width×300-μm height gap in which a calcium sensing element was subsequently formed as explained below. Measurements as explained in Example 3 were taken, assuming a normalised sensing element area of 1 m$^2$.

After the conductive track was fabricated, the test sample were rinsed with isopropyl alcohol (IPA) and blow-dried with nitrogen. The blow-dried substrates were then placed in a vacuum oven for degassing any absorbed moisture or oxygen. The pressure in the oven was set to $10^{-1}$ mbar and vacuum degassing was carried out for several hours at an elevated temperature of between 60-100° C., which is below the glass transition temperature of the polymer present in the barrier stack used in this example. The vacuum oven used here was additionally equipped with fore line traps to prevent the backflow of hydrocarbon oil from the vacuum pump to the vacuum oven.

Immediately after the degassing process, the partially formed sensor and test sample were transferred to a ULVAC SOLCIET Cluster Tool where plasma treatment was carried out for several hours. Radio frequency (RF) argon plasma was used to bombard the surface of the barrier film with low energy ions in order to remove surface contamination. The base pressure in the chamber was maintained below $4 \times 10^{-6}$ mbar. The argon flow rate was at 70 sccm and RF power was set at 200 W.

After the plasma treatment process, a liner layer comprising an acrylic polymer was deposited as a thin layer of about 100 nm by spin coating. The liner layer presents relatively little gas barrier properties, but ensures uniform layer-by-layer oxidation through the calcium sensing element.

After the deposition of the thin organic buffer layer, the test samples were transferred to a vacuum evaporation chamber. Subsequently, calcium was deposited through a suitable mask into the space between the two electrodes to form a 150 nm thick layer. After calcium deposition, a 100 nm insulating film comprising LiF was deposited by PVD onto the calcium.

Subsequently, the partially formed sensor was transferred to a glove box where it was encapsulated. UV curable epoxy was applied onto the rim of the test sample. A glass slide of matching dimension was placed onto the epoxy to seal off the calcium sensing element. A 400 W metal halide light source (2000-EC series UV light source, DYMAX Corporation) was used to cure the epoxy for about two minutes. The wavelengths of the light source was between 300 nm and 365 nm, with the respective intensities of 22 mW/cm$^2$ and 85 mW/cm$^2$. The entire encapsulation process was undertaken under inert nitrogen gas atmosphere in order to ensure optimum encapsulation.

EXAMPLE 3

Water Vapour Permeation Test Using 1/f Noise Measurement

The encapsulated sensor fabricated in Example 2 (cf. FIG. 9) which comprise the test sample comprising the barrier stack with silicon dioxide was transferred into a humidity chamber (WK1 Model, Weiss, Germany). A HP35670A digital signal analyser was connected to the electrodes to monitor the 1/f noise of the sensor. At the same time, a Keithley 24203A source meter was connected in parallel to the electrodes (cf. FIG. 9) to provide a constant current source to the sensor and to monitor the rate of change of calcium resistance over time. 1/f noise, calcium conductance and resistance measurements were done at a temperature of 40° C., 90% relative humidity and atmospheric pressure.

The graph of change in calcium resistance against time is shown in FIG. 10A. As can be seen from the figure, a lag time of about 2-3 hours is observed, during which the calcium sensor shows no degradation. This lag time represents the duration required for the water vapour to traverse the test sample before reaching the sensing element.

The graph of rate of change of calcium conductance against time as shown in FIG. 10B was also obtained. As can be seen from the figure, the time taken for calcium conductance to fall from the initial conductance is about 2.8 hours from the start of the test. Conductance decreases to zero in about 7 hours, meaning that about 4.2 hours was needed for the calcium sensing element to be completely consumed.

1/f noise measurements made by the digital signal analyser was plotted as a function of sensor resistance. The graph is shown in FIG. 10C.

Based on the data, the quantitative evaluation of water vapour transmission properties could be carried out as shown in the further examples below.

EXAMPLE 4

Calculation of Water Vapour Transmission Rate—Sensitivity of Noise Measurements This example describes a procedure for deriving water vapour transmission rate through a conventional barrier stack such as the one used in the above Example which is coated with silicon dioxide coating based on sensitivity of noise measurements according to the invention.

The data needed for carrying out the present calculations is taken from the resistance and noise measurements from Example 1. The time taken to oxidise 150 nm of calcium was about 4.2 hours as shown in the graph of FIG. 10B.

The 1/f noise analysis sensitivity of the digital signal analyzer (HP35670A) was specified to be less than $10^{-14}\ V^2_{rms}/Hz$ at 64 Hz & 1 mA constant current.

Using the data obtained from the measurements carried out in Example 1, the derivation of water vapour transmission rate was carried out as follows:

1) Rate of change of $1/f$ noise ($N$) in the sensor with respect to change of resistance ($R$) i.e. $(dN/dR) =$ Slope of graph of $1/f$ noise vs $R$ (Figure 10C) =

$3.38 \times 10^{-7}\ V^2_{rms}/Hz$ (at the value of $R = 23.13\ Ohms$)

Hence, for the change in resistance of 1Ω, there is a change of $3.38 \times 10^{-7}$ $V^2_{rms}$/Hz in the 1/f noise.

2) Conversely, for a change of $1 \times 10^{-14}$ $V^2_{rms}$/Hz in 1/f noise, the change in sensor resistance = $1 \times 10^{-14} \div 3.38 \times 10^{-7} = 2 \times 10^{-8}$ ohms.

3) For the change of $2 \times 10^{-8}$ ohms, the change in calcium thickness = $0.8 \times 10^{-5}$ nm.

4) Corresponding change in amount of Calcium (mol) =

$$\frac{\text{Volume} \times \text{Density}}{A_r(\text{Ca})} =$$

$$\frac{0.8 \times 10^{-14} m^3 \times 1.55 g/10^{-6} m^3}{40.08 \text{ g/mol}} =$$

$$3 \times 10^{-10} \text{ mol}$$

5) Two water molecules are required to react with one calcium atom. Hence, the number of moles of water molecules required to react with $3 \times 10^{-10}$ mol of Calcium =

$$2 \times 3 \times 10^{-10} \text{ mol} =$$

$$6 \times 10^{-10} \text{ mol}$$

6) The molecular weight of the $H_2O$ is 18 g/mol. Hence, the weight of $2.2 \times 10^{-10}$ mol of $H_2O$ =

$$6 \times 10^{-10} \text{ mol} \times 18 \text{ g/mol} \approx$$

$$1 \times 10^{-8} \text{ g/m}^2$$

Therefore, the sensitivity of the digital signal analyser for the detection of water vapour permeation is $1 \times 10^{-8}$ g/m².

7) Water vapour transmission rate (WVTR) =

$$1 \times 10^{-8} \text{ g/m}^2 \times (24 \text{ hrs/day} \div 4.2 \text{ hrs}) \approx$$

$$5.71 \times 10^{-8} \text{ g/m}^2/\text{day}$$

From the above, it can be seen that the sensitivity of noise measurement method is able to measure a water vapour transmission rate of less than $10^{-6}$ g/m²/day and is therefore sufficiently sensitive for the measurement of low gas transmission rates.

EXAMPLE 5

Calculation of Water Vapour Transmission Rate—Direct Measurement of Calcium Resistance The present example describes a method of deriving water vapour transmission rate based on direct measurements of calcium electrical resistance.

The data needed for carrying out the present calculations is taken from the resistance and noise measurements from Example 2. The time taken to oxidise 150 nm of calcium was about 4.2 hours as shown in the graphs of FIGS. 10A and 10B.

The derivation of water vapour transmission rate was carried out as follows:

1) Amount of Calcium (mol) reacted when conductance falls to 0 Mho, (i.e. calcium sensor is completely reacted) =

$$\frac{\text{Volume} \times \text{Density}}{A_r(\text{Ca})} =$$

$$\frac{150 \times 10^{-9} m^3 \times 1.55 g/10^{-6} m^3}{A_r(\text{Calcium}) \text{ g/mol}} =$$

$$5.8 \times 10^{-3} \text{ mol}$$

2) Two water molecules are required to react with one calcium atom. Hence, the number of moles of water molecules required to react with $5.8 \times 10^{-3}$ mol of calcium =

$$2 \times 5.8 \times 10^{-3} \text{ mol} =$$

$$11.6 \times 10^{-3} \text{ mol}$$

6) The molecular weight of the $H_2O$ is 18 g/mol. Hence, the weight of $11.6 \times 10^{-3}$ mol of $H_2O$ =

$$11.6 \times 10^{-3} \text{ mol} \times 18 \text{ g/mol} =$$

$$0.208 \text{ g/m}^2 \approx$$

$$0.2 \text{ g/m}^2$$

Therefore, the achievable sensitivity based on the direct measurement of calcium resistance is 0.2 g/m².

7) Water vapour transmission rate (WVTR) =

$$0.2 \text{ g/m}^2 \times (24 \text{ hrs/day} \div 4.2 \text{ hrs}) \approx$$

$$1.1 \text{ g/m}^2 \cdot \text{day}$$

Accordingly, the direct resistance method can also be used with the present sensor to calculate gas transmission rate. However, in this specific experimental setup, the direct resistance measurement method is not suitable for determining a gas transmission rate of less than $10^{-6}$ g/m²/day.

EXAMPLE 6

Calculation of Water Vapour Transmission Rate—Sensitivity of Resistance Measurements The present example shows a method of deriving the water vapour transmission rate based on sensitivity of resistance measurements using a Keithley 24203A source meter. The data that is required for calculation purposes were obtained from the measurements carried out in Example 1. The sensitivity of the source meter was specified to be about 1 mΩ.

The derivation of water vapour transmission rate was carried out as follows:

1) The change in calcium sensor thickness ($\Delta t$) with respect to $1\,m\Omega$ change in resistance ($\Delta R$) =

$$\frac{\Delta R}{R} = \frac{1\,m\Omega}{.37\,\Omega} = 2.7 \times 10^{-3} = \frac{\Delta t}{t} = \frac{\Delta t}{150\,nm} = 0.4\,nm$$

2) Change in amount of Calcium (mol) for the change in $$1\,m\Omega = \frac{\text{Volume} \times \text{Density}}{A_r(\text{Ca})} =$$

$$\frac{0.4 \times 10^{-9} m^3 \times 1.55\,g/10^{-6} m^3}{40.08\,g/mol} =$$

$$1.55 \times 10^{-5}\,mol$$

3) Two water molecules are required to react with one calcium atom. Hence, the number of moles of water molecules required to react with $1.55 \times 10^{-5}$ mol of calcium =

$2 \times 1.55 \times 10^{-5}\,mol =$ $3.1 \times 10^{-5}\,mol$

4) The molecular weight of the $H_2O$ is 18 g/mol. Hence, the weight of $3.1 \times 10^{-5}$ mol of $H_2O$ =

$3.1 \times 10^{-5}\,mol \times 18\,g/mol \approx$ $5 \times 10^{-3}\,g/m^2$

Therefore, the sensitivity of the digital signal analyser for the detection of water vapour permeation is $5 \times 10^{-3}\,g/m^2$.

5) Water vapour transmission rate (WVTR) =

$5 \times 10^{-3}\,g/m^2 \times (24\,hrs/day \div 4.2\,hrs) \approx$ $2.9 \times 10^{-2}\,g/m^2/day$ Accordingly, the direct resistance method can also be used with the present sensor to calculate gas transmission rate. However, in this specific experimental setup, the sensitivity of resistance measurements was not able to determine a gas transmission rate of less than $10^6\,g/m^2/day$.

EXAMPLE 7

Estimation of Diffusion Coefficient

Extrapolating the curve in the steady state region of FIG. 10A to zero provides the lag time (L), which can be related to the elapsed time before steady state according to formula (V):

$$L = \frac{l^2}{6D}$$

The barrier-coated polymer substrates are either assumed to be a homogeneous single substrate or the oxide layer is considered to be the barrier layer since the base polymer substrate provides only 3% of resistance. The time lag technique is used to determine diffusion coefficient. The necessary boundary conditions are the following: an initially gas free film, attainment of equilibrium at the gas-polymer interface, and zero concentration of gas at the calcium side. Under these conditions, using the lag time L method, it is possible to calculate the diffusion co-efficient for the required barrier film with the following equation, where L is the lag time, l is the thickness of the barrier layer; D is the diffusion coefficient ($m^2/s$).

The data needed for carrying out the present calculations is taken from the resistance and noise measurements from Example 2. The time taken to oxidise 150 nm of calcium was about 4.2 hours as shown in the graphs of FIGS. 10A and 10B.

Therefore, the lag time (L) is 4.2 hours and silicon oxide coated polycarbonate barrier stack total thickness is 175 micron, hence, the diffusion coefficient (D) will be:

$$D = \frac{(175\,\mu m)^2}{6 \times 4.2 \times 60 \times 60\,s}$$

$$= \frac{30625\,(\mu m)^2}{90720\,s}$$

$$= 3.4 \times 10^{-13}\,m^2/s$$

Hence, the diffusion coefficient D for the given silicon oxide coated substrate is $3.4 \times 10^{-13}\,m^2/s$.

EXAMPLE 8

Estimation of Permeability Coefficient (P)

The rate of gas or vapour transfer through the membrane in the steady state is usually calculated according to formula (VI):

$$WVTR = \frac{P_{(p_1-p_2)}}{l}$$

where WVTR is water vapour transmission rate in given time [$g/m^2.day$], P is permeability coefficient [$g.\mu m/m^2.day.bar$], $p_1$ is a pressure on the high pressure side of the barrier stack, $p_2$ is a pressure on the low pressure side of the barrier stack, and l is path length ($\mu m$) for diffusion (thickness of the barrier stack).

The data needed for carrying out the present calculations was taken from the resistance and noise measurements from Example 2. The time taken to oxidise 150 nm of calcium was about 4.2 hours as shown in the graphs of FIGS. 10A and 10B.

The water vapour transmission rate calculated from the example 5 is 1.1 $g/m^2/day$. The total thickness of the barrier stack is 175 micron, $p_1$=55 mbar (vapor pressure in the humidity chamber at 90% relative humidity), $p_2$=0 [vapour pressure inside calcium encapsulated test barrier stack is close to zero since all the water vapor would react with calcium].

Applying the values into the above permeability coefficient equation:

$$P = \frac{WVTR \times l}{p_1 - p_2} \Rightarrow \frac{192.5\,g.\mu m/m^2.day}{0.055\,bar - 0} \Rightarrow 3.5 \times 10^3\,g.\mu m/m^2.day\; @\; 40°C.\; \&\; 90\%\; RH$$

Hence, the permeability coefficient (P) for the given silicon oxide coated substrate is $3.5 \times 10^3$ g.μm/m².day at one bar with 40° C. & 90% RH conditions.

EXAMPLE 9

Study of the Effect of a Liner Layer on Sensor Degradation Pattern

In the present example, test were carried out on polymer substrates to study the effect which a liner layer has on the degradation pattern of the sensing element.

A sensor comprising a calcium sensing element was fabricated on a PET substrate which had a metal oxide barrier coating according to the procedure described in Example 1. A 100 nm thick acrylic polymer liner was applied onto the surface of the metal oxide coating. The sensor was encapsulated in a similar way to an OLED package, as shown in FIG. 6. A control was fabricated without incorporating an liner layer. The test on both test specimens was carried out in a humidity chamber at 50° C. temperature and 90% relative humidity.

The images as shown in FIGS. 11A and 11B were taken at intervals of several hours into the test. Calcium degradation was monitored through an optical microscope and digital images were taken from five locations on the surface of the sensing element. FIG. 11A shows the uniform degradation of the sensing element as the test progressed. In comparison, FIG. 11B shows that the sensing element in the control was degraded non-uniformly.

From these results, it can be seen that a uniform, layer-by-layer degradation of the sensing element in the sensor was facilitated by the liner layer.

EXAMPLE 10

Study of the Effect of a Non-Inorganic Terminating Layer on Sensor Degradation Pattern When Test Material is Glass In the present example, a test using a sensor of the invention was carried out on a glass substrate. The purpose is to study the uniformity of degradation in the sensor.

A sensor was fabricated onto a glass substrate according to the procedure described in Example 1. No liner layer was applied onto the surface of the glass substrate. The sensor was designed to have a similar layout as an OLED package structure shown in FIG. 6. The sensor was encapsulated with adhesive material and a glass cover substrate. The test was carried out in a humidity chamber at 50° C. temperature and 90% relative humidity. As water vapour penetrated through the adhesive material, the sensing element was gradually degraded. The sensor was monitored through an optical microscope. Digital images were taken from 5 defined locations for each measurement at intervals of several hours (cf. FIG. 12A). The images show that the degradation of the sensing element is uniform in an OLED package.

The optical properties of the calcium sensor were monitored using a UV-3101 PC UV-VIS-NIR scanning spectrophotometer from SHIMADZU. FIG. 12B shows the graph of reflectivity of the calcium sensor as measured at intervals of several hours on 5 different locations on the sensing element. It can be seen from the graph that the measured reflectance at each location of sensor remains same and does not show any substantial variation. Therefore, calcium oxidation appears to be uniform across the sensor and the drop in reflectance confirms that the dynamics of calcium oxidation occurs in a layer-by-layer progression.

It can be seen that the calcium sensing element fabricated using an OLED package structure is oxidized uniformly and in a layer-by-layer progression. Accordingly, the decrease in electrical conductivity of the sensor can be correlated to the corresponding decrease in thickness of the sensing element.

EXAMPLE 11

Measurement of Combined Oxygen and Water Vapour Permeation Properties Through a Test Material The present invention can be carried out not only in a humidity chamber but also in a custom made test cell. The present invention allows the measurement of permeation of oxygen, water vapour, or any other gas, through any test substrate or package can be carried out in a single test chamber. In addition, the measurement can be carried out at elevated temperatures and pressures.

FIG. 13 depicts a test cell which comprises a conventional gas chamber provided with 2 pairs of gas inlets and outlets. The chamber comprises a test specimen clamping section located at the middle portion of the chamber. In order to carry out a measurement in the test chamber, the test material is first cut according to required the dimensions. The sensor is fabricated without an encapsulation onto the test material according to a method described above. When the test specimen is inserted into the chamber and clamped at the clamping section, the chamber is divided into 2 portions, A and B. A gas mixture having a composition that simulates the required test conditions is prepared and channelled into chamber A. The gas mixture enters the chamber via the inlet and is evacuated via the outlet. If necessary, Chamber B is provided with an inert environment by circulating dry nitrogen gas into the chamber. This may also serve to flush out any reactive gas that permeates into Chamber B. A suitable RH probe monitors the relative humidity.

A suitable electrical feed-through can be used to connect the conductive track to measure resistance and 1/f noise spectrum. The water or oxygen molecule that permeated through low gas permeability test substrate reacts with the calcium sensor. Constant source meter and digital signal analyzer can measure the resistance and 1/f noise spectrum respectively. The rate of change of resistance and noise characteristics can be used to calculate water vapour or oxygen transport properties of the test film.

What is claimed is:

1. A sensor for measuring gas permeability of a test material, comprising:
   an electrically conductive sensing element that comprises a water and/or oxygen sensitive material, wherein the reaction of said material with water or oxygen when the sensing element is contacted with water and/or oxygen results in a change in the electrical conductivity of the sensing element, wherein the water and/or oxygen sensitive material is selected from the group consisting of metals of Group I of the periodic system of elements, metals of Group II of the periodic system of elements, iron, tin, chromium, conductive polymers, and mixtures and combinations thereof;
   two electrodes electrically connected to the sensing element;
   a base substrate that supports the sensing element, wherein the electrodes are located on a surface of the substrate, wherein the electrodes are spaced apart, thereby forming a trench, wherein edges of the trench are defined by the edge of each electrode and the base of the trench is the base substrate, wherein the sensing element is located in the trench; and a liner layer interdisposed between the sensing element and the base substrate, wherein the liner layer adjoins the sensing element, and wherein the liner layer comprises an organic polymer and/or an inorganic polymer.

2. The sensor of claim 1, wherein the electrodes provide electrical connection between the sensing element and an electrical signal evaluation means.

3. The sensor of claim 1, wherein the water and/or oxygen sensitive material is selected from the group consisting of calcium and magnesium.

4. The sensor of claim 1, wherein the conductive polymer is selected from the group consisting of polyaniline, polypyrrole and polythiophene, polyacetylene, poly-p-phenylene, and polyvinylpyridine, thiophene-bipyridine copolymers, polypyridine, polybipyridine, and organometallic polyphenylenes.

5. The sensor of claim 1, wherein the electrodes comprise an electrically conductive material selected from the group consisting of a metal, metal oxide and mixtures and combinations thereof.

6. The sensor of claim 5, wherein the metal is selected from the group consisting of silver, gold, aluminium and copper.

7. The sensor of claim 5, wherein the metal oxide is selected from the group consisting of indium tin oxide, aluminium zinc oxide, and indium zinc oxide.

8. The sensor of claim 7, wherein the base substrate comprises a polymeric material.

9. The sensor of claim 8, wherein the polymeric material comprises an organic polymer selected from the group consisting of polycarbonate, polyethylene, polythersulfone, epoxy resins, polyethylene terephthalate, polystyrenes, polyurethanes and polyacrylates.

10. The sensor of claim 8, wherein the polymeric material comprises an inorganic polymer selected from the group consisting of silicones, polydimethylsiloxanes, biscyclopentadienyl iron, polydichlorophosphazene and derivatives thereof.

11. The sensor of claim 7, further comprising a barrier layer formed on the base substrate.

12. The sensor of claim 11, wherein the barrier layer comprises a material selected from the group consisting of metals, metal oxides, ceramic oxides, inorganic polymers, organic polymers and mixtures and combinations thereof.

13. The sensor of claim 1, further comprising an encapsulation enclosing the sensing element.

14. The sensor of claim 13, wherein the encapsulation comprises a polymeric material selected from the group consisting of epoxy polymers, polysulfide, silicone and polyurethane.

15. The sensor of claim 14, wherein the encapsulation provides a hollow space around the sensing element.

16. The sensor of claim 15, wherein the hollow space is filled with an inert gas.

17. The sensor of claim 13, further comprising a cover substrate, wherein the encapsulation is formed as side (lateral) walls surrounding the sensing element, and the cover substrate is arranged to be in contact with the side (lateral) walls.

18. The sensor of claim 17, wherein the cover substrate comprises a material selected from the group consisting of glass, aluminium and copper.

19. The sensor of claim 1, further comprising a protective layer covering at least a portion of the sensing element.

20. The sensor of claim 19, wherein the protective layer comprises a material selected from the group consisting of a metal, a metal alloy, a metal oxide, a metal oxide mixture, a metal fluoride and an organic polymer.

21. The sensor of claim 20, wherein the metal fluoride is selected from the group consisting of LiF and $MgF_2$.

22. The sensor of claim 1, wherein the organic polymer is substantially permeable to gas.

23. The sensor of claim 1, wherein the organic polymer is selected from the group consisting of acrylic polymers, and parylene type polymers.

24. The sensor of claim 1, wherein the inorganic polymer comprises a silicone-based polymer.

25. A method of producing a sensor for measuring gas permeability of a test material, said method comprising:

providing a base substrate that supports a sensing element and that further comprises a liner layer, wherein the liner layer comprises an organic polymer and/or an inorganic polymer;

depositing on the liner layer an electrically conducting sensing element that comprises a water and/or oxygen sensitive material selected from the group consisting of metals of Group I of the periodic system of elements, metals of Group II of the periodic system of elements, iron, tin, chromium, conductive polymers, and mixtures and combinations thereof, so that the liner layer is interdisposed between the base substrate and the sensing element and the liner layer adjoins the sensing element;

providing two electrodes, wherein the electrodes are located on a surface of the substrate, wherein the electrodes are spaced apart, thereby forming a trench, wherein edges of the trench are defined by the edge of each electrode and the base of the trench is the base substrate, wherein the sensing element is located in the trench; and connecting the electrically conductive sensing element to said pair of electrodes.

26. A system for measuring the gas permeability of a test material, said system comprising a sensor for detecting moisture permeation through the test material, said sensor comprising:

an electrically conductive sensing element that comprises a water and/or oxygen sensitive material selected from the group consisting of metals of Group I of the periodic system of elements, metals of Group II of the periodic system of elements, iron, tin, chromium, conductive polymers, and mixtures and combinations thereof, wherein the reaction of said material with water or oxygen when the sensing element is contacted with water and/or oxygen results in a change in the electrical conductivity of the sensing element;

two electrodes electrically connected to the sensing element, wherein the electrodes provide electrical connection between the sensing element and an electrical signal evaluation means;

a base substrate that supports the sensing element, wherein the electrodes are located on a surface of the substrate, wherein the electrodes are spaced apart, thereby forming a trench, wherein edges of the trench are defined by the edge of each electrode and the base of the trench is the base substrate, wherein the sensing element is located in the trench; and a liner layer interdisposed between the sensing element and the base substrate, wherein the liner layer adjoins the sensing element, and wherein the liner layer comprises an organic polymer and/or an inorganic polymer.

27. A method of determining the gas permeability of a test material using a sensor for measuring gas permeability of the test material, said sensor comprising:
- an electrically conductive sensing element that comprises a water and/or oxygen sensitive material selected from the group consisting of metals of Group I of the periodic system of elements, metals of Group II of the periodic system of elements, iron, tin, chromium, conductive polymers, and mixtures and combinations thereof, wherein the reaction of said material with water or oxygen when the sensing element is contacted with water and/or oxygen results in a change in the electrical conductivity of the sensing element;
- two electrodes electrically connected to the sensing element, wherein the electrodes provide electrical connection between the sensing element and an electrical signal evaluation means;
- a base substrate that supports the sensing element, wherein the electrodes are located on a surface of the substrate, wherein the electrodes are spaced apart, thereby forming a trench, wherein edges of the trench are defined by the edge of each electrode and the base of the trench is the base substrate, wherein the sensing element is located in the trench; and
- a liner layer interdisposed between the sensing element and the base substrate, wherein the liner layer adjoins the sensing element, and wherein the liner layer comprises an organic polymer and/or an inorganic polymer;

wherein said method comprises:

contacting the sensing element with water and/or oxygen;

measuring the changes in electrical conductivity of the sensing element over a period of time; and calculating the gas permeability coefficient of the test material based on the measurements.

28. The method of claim 27, further comprising measuring the change in $1/f$ type noise spectrum density over the period of time.

UNITED STATES PATENT AND TRADEMARK OFFICE
CERTIFICATE OF CORRECTION

| | | |
|---|---|---|
| PATENT NO. | : 8,603,825 B2 | Page 1 of 1 |
| APPLICATION NO. | : 10/594789 | |
| DATED | : December 10, 2013 | |
| INVENTOR(S) | : Soo Jin Chua | |

It is certified that error appears in the above-identified patent and that said Letters Patent is hereby corrected as shown below:

In the Specifications

Column 5, line 4:
"...resistance of 3.41Ω-cm..."
should be
--...resistance of 3.4μΩ-cm...--

Signed and Sealed this
Twenty-fifth Day of March, 2014

Michelle K. Lee
*Deputy Director of the United States Patent and Trademark Office*